(12) United States Patent
Maharbiz et al.

(10) Patent No.: US 12,233,269 B2
(45) Date of Patent: Feb. 25, 2025

(54) POWER CONTROLS FOR AN IMPLANTABLE DEVICE POWERED USING ULTRASONIC WAVES

(71) Applicant: Iota Biosciences, Inc., Alameda, CA (US)

(72) Inventors: Michel M. Maharbiz, El Cerrito, CA (US); Joshua Kay, Oakland, CA (US); Jose M. Carmena, Alameda, CA (US)

(73) Assignee: IOTA BIOSCIENCES, INC., Alameda, CA (US)

( * ) Notice: Subject to any disclaimer, the term of this patent is extended or adjusted under 35 U.S.C. 154(b) by 697 days.

(21) Appl. No.: 17/420,336

(22) PCT Filed: Jan. 3, 2020

(86) PCT No.: PCT/US2020/012248
§ 371 (c)(1),
(2) Date: Jul. 1, 2021

(87) PCT Pub. No.: WO2020/142733
PCT Pub. Date: Jul. 9, 2020

(65) Prior Publication Data
US 2022/0062650 A1    Mar. 3, 2022

Related U.S. Application Data

(60) Provisional application No. 62/788,405, filed on Jan. 4, 2019.

(51) Int. Cl.
*A61N 1/378*    (2006.01)
*A61B 5/24*     (2021.01)
(Continued)

(52) U.S. Cl.
CPC .............. *A61N 1/3787* (2013.01); *A61B 5/24* (2021.01); *A61N 1/08* (2013.01); *A61N 1/36053* (2013.01);
(Continued)

(58) Field of Classification Search
CPC .... A61N 1/3787; A61N 1/08; A61N 1/36053; A61N 1/36128; A61N 1/37276; H02J 50/15
See application file for complete search history.

(56) References Cited

U.S. PATENT DOCUMENTS

| 5,107,833 A | 4/1992 | Barsness |
| 5,331,966 A | 7/1994 | Bennett |

(Continued)

FOREIGN PATENT DOCUMENTS

| CN | 101612451 A | 12/2009 |
| CN | 102427849 A | 4/2012 |

(Continued)

OTHER PUBLICATIONS

Arbabian, A. et al. (Dec. 1, 2016, e-pub. Nov. 11, 2016). "Sound Technologies, Sound Bodies: Medical Implants With Ultrasonic Links," IEEE Microwave Magazine 17(12):39-54.

(Continued)

*Primary Examiner* — Mallika D Fairchild
(74) *Attorney, Agent, or Firm* — MORRISON & FOERSTER LLP

(57) ABSTRACT

Method and system embodiments for controlling power provided to a device implantable in a subject are described. In some embodiments, a method is performed at the implantable device to receive, from an interrogator, powering ultrasonic waves having a wave power. Then, energy from the powering ultrasonic waves is converted into an electrical signal to power the implantable device. Information that (Continued)

indicates whether more power or less power should be transmitted to the implantable device is transmitted to the interrogator.

25 Claims, 5 Drawing Sheets

(51) Int. Cl.
*A61N 1/08* (2006.01)
*A61N 1/36* (2006.01)
*A61N 1/372* (2006.01)
*H02J 50/15* (2016.01)

(52) U.S. Cl.
CPC ..... *A61N 1/36128* (2013.01); *A61N 1/37276* (2013.01); *H02J 50/15* (2016.02)

(56) References Cited

U.S. PATENT DOCUMENTS

| | | | |
|---|---|---|---|
| 5,693,076 | A | 12/1997 | Kaemmerer |
| 6,170,488 | B1 | 1/2001 | Spillman, Jr. |
| 6,185,452 | B1 | 2/2001 | Schulman et al. |
| 6,480,743 | B1 | 11/2002 | Kirkpatrick |
| 7,069,086 | B2 | 6/2006 | Von |
| RE42,934 | E | 11/2011 | Thompson |
| 8,214,164 | B2 * | 7/2012 | Gandhi ............ A61N 1/3708 320/132 |
| 8,301,262 | B2 | 10/2012 | Mi et al. |
| 8,786,134 | B2 | 7/2014 | Kazama |
| 9,544,068 | B2 | 1/2017 | Arbabian |
| 9,731,141 | B2 * | 8/2017 | Tran .................... A61N 1/3787 |
| 10,014,570 | B2 | 7/2018 | Arbabian |
| 10,118,054 | B2 | 11/2018 | Maharbiz |
| 10,177,606 | B2 | 1/2019 | Charthad |
| 10,300,309 | B2 | 5/2019 | Maharbiz |
| 10,300,310 | B2 | 5/2019 | Maharbiz |
| 10,576,305 | B2 | 3/2020 | Maharbiz |
| 10,682,530 | B2 | 6/2020 | Maharbiz |
| 10,744,347 | B2 | 8/2020 | Maharbiz |
| 10,765,865 | B2 | 9/2020 | Maharbiz |
| 10,898,736 | B2 | 1/2021 | Maharbiz et al. |
| 11,033,746 | B2 | 6/2021 | Maharbiz et al. |
| 11,246,990 | B2 | 2/2022 | Brauker |
| 11,589,748 | B2 | 2/2023 | Maharbiz |
| 11,601,019 | B2 | 3/2023 | Arbabian |
| 11,607,128 | B2 | 3/2023 | Maharbiz |
| 11,717,689 | B2 | 8/2023 | Maharbiz et al. |
| 11,786,124 | B2 | 10/2023 | Maharbiz et al. |
| 11,890,474 | B2 | 2/2024 | Carmena |
| 11,969,596 | B2 | 4/2024 | Carmena |
| 12,004,840 | B2 | 6/2024 | Maharbiz |
| 2002/0013612 | A1 | 1/2002 | Whitehurst |
| 2002/0156504 | A1 | 10/2002 | Chen |
| 2003/0060163 | A1 | 3/2003 | Filkins |
| 2003/0229383 | A1 | 12/2003 | Whitehurst |
| 2004/0030260 | A1 | 2/2004 | Arx |
| 2004/0106967 | A1 | 6/2004 | Von |
| 2004/0147969 | A1 | 7/2004 | Mann |
| 2006/0122663 | A1 | 6/2006 | Mandell |
| 2006/0136004 | A1 | 6/2006 | Cowan |
| 2006/0149324 | A1 | 7/2006 | Mann |
| 2006/0265022 | A1 | 11/2006 | John et al. |
| 2007/0078490 | A1 | 4/2007 | Cowan |
| 2007/0150019 | A1 | 6/2007 | Youker |
| 2008/0228090 | A1 | 9/2008 | Wariar |
| 2009/0024054 | A1 | 1/2009 | Lazarus |
| 2009/0124875 | A1 | 5/2009 | Bentsen |
| 2009/0138058 | A1 | 5/2009 | Cooke |
| 2009/0157144 | A1 | 6/2009 | Kelly |
| 2009/0198307 | A1 | 8/2009 | Mi et al. |
| 2009/0222065 | A1 | 9/2009 | Dlugos, Jr. |
| 2010/0131033 | A1 | 5/2010 | Cantatore |
| 2012/0169336 | A1 | 7/2012 | Leigh |
| 2013/0027186 | A1 | 1/2013 | Cinbis |
| 2013/0046354 | A1 | 2/2013 | Frustaci |
| 2013/0172774 | A1 | 7/2013 | Crowder |
| 2013/0218251 | A1 | 8/2013 | Penner |
| 2014/0200638 | A1 | 7/2014 | Chow |
| 2014/0336474 | A1 | 11/2014 | Arbabian |
| 2015/0012057 | A1 | 1/2015 | Carlson |
| 2016/0015986 | A1 | 1/2016 | Seeberger |
| 2016/0156229 | A1 | 6/2016 | Sakata |
| 2016/0250486 | A1 | 9/2016 | Yoder |
| 2017/0064462 | A1 | 3/2017 | Warren |
| 2017/0117753 | A1 | 4/2017 | Charthad |
| 2017/0125892 | A1 | 5/2017 | Arbabian |
| 2017/0135633 | A1 | 5/2017 | Connor |
| 2017/0201130 | A1 * | 7/2017 | Park ................... H02J 50/80 |
| 2017/0312530 | A1 | 11/2017 | Schilling |
| 2017/0319858 | A1 | 11/2017 | Radziemski et al. |
| 2018/0000344 | A1 | 1/2018 | Melodia |
| 2018/0027077 | A1 | 1/2018 | Melodia |
| 2018/0085605 | A1 | 3/2018 | Maharbiz |
| 2019/0022427 | A1 | 1/2019 | Maharbiz |
| 2019/0022428 | A1 | 1/2019 | Maharbiz |
| 2019/0150881 | A1 | 5/2019 | Maharbiz |
| 2019/0150882 | A1 | 5/2019 | Maharbiz |
| 2019/0150883 | A1 | 5/2019 | Maharbiz |
| 2019/0150884 | A1 | 5/2019 | Maharbiz |
| 2019/0321640 | A1 | 10/2019 | Carmena |
| 2019/0321644 | A1 | 10/2019 | Maharbiz |
| 2019/0358460 | A1 * | 11/2019 | Alford ................. A61B 5/7228 |
| 2020/0023208 | A1 | 1/2020 | Maharbiz |
| 2020/0023209 | A1 | 1/2020 | Maharbiz |
| 2020/0105151 | A1 | 4/2020 | Mahkonen |
| 2020/0114175 | A1 | 4/2020 | Maharbiz |
| 2020/0230441 | A1 | 7/2020 | Maharbiz |
| 2020/0252730 | A1 | 8/2020 | Frieding |
| 2020/0257136 | A1 | 8/2020 | Arbabian et al. |
| 2020/0289857 | A1 | 9/2020 | Maharbiz |
| 2020/0324148 | A1 | 10/2020 | Maharbiz |
| 2020/0327975 | A1 | 10/2020 | Barthelaix |
| 2021/0146144 | A1 | 5/2021 | Jimenez |
| 2021/0268294 | A1 | 9/2021 | Maharbiz et al. |
| 2021/0308462 | A1 | 10/2021 | Carmena et al. |
| 2021/0392720 | A1 | 12/2021 | Fang |
| 2022/0047869 | A1 | 2/2022 | Carmena et al. |
| 2022/0143414 | A1 | 5/2022 | Maharbiz et al. |
| 2022/0387791 | A1 | 12/2022 | Bakker |
| 2023/0089015 | A1 | 3/2023 | Maharbiz et al. |
| 2023/0095948 | A1 | 3/2023 | Maharbiz et al. |
| 2023/0233851 | A1 | 7/2023 | Neely et al. |
| 2023/0301514 | A1 | 9/2023 | Lepe et al. |
| 2023/0414950 | A1 | 12/2023 | Maharbiz |
| 2024/0017071 | A1 | 1/2024 | Carmena |
| 2024/0024032 | A1 | 1/2024 | Kay |
| 2024/0099584 | A1 | 3/2024 | Maharbiz |
| 2024/0100327 | A1 | 3/2024 | Carmena |
| 2024/0108882 | A1 | 4/2024 | Maharbiz |
| 2024/0148250 | A1 | 5/2024 | Maharbiz |

FOREIGN PATENT DOCUMENTS

| | | |
|---|---|---|
| CN | 103079633 A | 5/2013 |
| CN | 108136439 A | 6/2018 |
| CN | 108430570 A | 8/2018 |
| CN | 108604824 A | 9/2018 |
| JP | 2005535391 A | 11/2005 |
| JP | 2007313336 A | 12/2007 |
| JP | 2010239781 A | 10/2010 |
| JP | 2011508871 A | 3/2011 |
| JP | 2016512677 A | 4/2016 |
| JP | 2019524224 A | 9/2019 |
| JP | 2019524230 A | 9/2019 |
| JP | 2019527568 A | 10/2019 |
| JP | 2020500048 A | 1/2020 |
| WO | 200232502 A1 | 4/2002 |
| WO | 2010131157 A1 | 11/2010 |
| WO | 2011112773 A2 | 9/2011 |
| WO | 2014121296 A1 | 8/2014 |
| WO | 2014174790 A1 | 10/2014 |
| WO | 2015142842 A2 | 9/2015 |

(56) References Cited

FOREIGN PATENT DOCUMENTS

| | | |
|---|---|---|
| WO | 2015142842 A3 | 11/2015 |
| WO | 2017015506 A1 | 1/2017 |
| WO | 2017116752 A1 | 7/2017 |
| WO | 2017120560 A1 | 7/2017 |
| WO | 2018009905 A2 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018009905 A3 | 2/2018 |
| WO | 2018081793 A1 | 5/2018 |
| WO | 2019075203 A1 | 4/2019 |
| WO | 2019204769 A1 | 10/2019 |
| WO | 2019204773 A1 | 10/2019 |
| WO | 2020047152 A1 | 3/2020 |
| WO | 2020117967 A1 | 6/2020 |
| WO | 2020142732 A1 | 7/2020 |
| WO | 2020142733 A1 | 7/2020 |
| WO | 2021077020 A1 | 4/2021 |
| WO | 2021077022 A1 | 4/2021 |
| WO | 2021168163 A1 | 8/2021 |
| WO | 2021168229 A1 | 8/2021 |
| WO | 2021248013 A1 | 12/2021 |
| WO | 2022035889 A1 | 2/2022 |
| WO | 2022046770 A1 | 3/2022 |
| WO | 2023183891 A2 | 9/2023 |
| WO | 2024011141 A2 | 1/2024 |
| WO | 2024086662 A1 | 4/2024 |
| WO | 2024167868 A2 | 8/2024 |
| WO | 2024182632 A2 | 9/2024 |

OTHER PUBLICATIONS

Bertrand, A. et al. (Aug. 2014). "Beamforming Approaches for Untethered, Ultrasonic Neural Dust Motes for Cortical Recording: A Simulation Study," IEEE EMBC, 2625-2628.

Grossman, N. et al. (Jun. 1, 2017). "Noninvasive Deep Brain Stimulation via Temporally Interfering Electric Fields," Cell 169:1029-1041.

International Preliminary Report on Patentability, issued Jun. 16, 2021 for PCT Application No. PCT/US2020/012248, filed Jan. 3, 2020, 16 pages.

International Search Report and Written Opinion, mailed Mar. 16, 2020, for PCT Application No. PCT/US2020/012248, filed Jan. 3, 2020, 18 pages.

Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp. 1-11.

Shmilovitz et al. (Apr. 2014). "Noninvasive Control of the Power Transferred to an Implanted Device by an Ultrasonic Transcutaneous Energy Transfer Link," IEEE Transaction on Bio medical Engineering 61(4):1-10.

Taylor, J. et al. (2004). "Multiple-Electrode Nerve Cuffs for Low-Velocity and Velocity-Selective Neural Recording," Medical & Biological Engineering & Computing 42:634-643.

U.S. Appl. No. 18/099,882, Maharbiz et al., filed Jan. 20, 2023. (Copy not submitted herewith pursuant of the waiver of 37 C.F.R. 1.98(a)(2)(iii) issued by the Office on Sep. 21, 2004).

U.S. Appl. No. 18/111,499, Maharbiz et al., filed Feb. 17, 2023. (Copy not submitted herewith pursuant to the waiver of 37 C.F.R. § 1.98(a)(2)(iii) issued by the Office on Sep. 21, 2004).

U.S. Appl. No. 18/414,173, Carmena et al., filed Jan. 16, 2024. (Copy not submitted herewith pursuant to the waiver of 37 C.F.R. § 1.98(a)(2)(iii) issued by the Office on Sep. 21, 2004).

Wodlinger, B. et al. (Oct. 2009). "Localization and Recovery of Peripheral Neural Sources With Beamforming Algorithms," IEEE Transactions on Neural Systems and Rehabilitation Engineering 17(5):461-468, 18 pages.

Bin, Y. (2006). "7.3 The Operating Modes and Programming of 8253," in Microcomputer Principles and Interface Technology, Southwest Jiaotong University Press, Chengdu, China, 24 pages. (English Translation).

Ji, Y. (2011). "6.5.7 Fieldbus Drive," in CNC System Software Design Based on Industrial Control Programming Language IEC6113-3, Beijing University of Aeronautics and Astronautics Press, Beijing, China, 16 pages. (English Translation).

* cited by examiner

POWER CONTROLS FOR AN IMPLANTABLE DEVICE POWERED USING ULTRASONIC WAVES

CROSS-REFERENCE TO RELATED APPLICATION

This application is a U.S. national phase application under 35 U.S.C. § 371 of International Application No. PCT/US2020/012248, filed on Jan. 3, 2020, which claims priority benefit to U.S. Provisional Application No. 62/788,405, filed on Jan. 4, 2019, the entire disclosure of each of which is incorporated herein by reference for all purposes.

FIELD OF THE DISCLOSURE

The present disclosure relates generally to an implantable device and, more specifically, an implantable device powered using ultrasonic waves.

BACKGROUND OF THE DISCLOSURE

Invasive methods have been developed for treating various medical conditions of a patient. These methods may involve inserting an implantable medical device (IMD) such as a cardiac or neural bio-implant within the patient's body. Powering such implantable devices remains a technical challenge for many biomedical applications. This is, in part, because the traditional approach of using batteries such as lithium batteries to power an implantable device renders the implantable device too large to be safely and comfortably placed at many locations in the body, thereby limiting the feasibly of many biomedical applications. Moreover, batteries typically produce power based on reacting chemicals, many of which are toxic and may pose a health hazard for the patient.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE DISCLOSURE

As discussed above, there is a need for implantable devices having a smaller form factor (e.g., in mm and sub-mm dimensions) to increase biocompatibility and reduce the invasiveness and discomfort caused by larger implantable devices powered using, for example, lithium batteries. In some embodiments, to achieve this smaller form factor, an implantable device can be configured to be powered using ultrasonic waves receivable at one or more ultrasonic transducers of the implantable device.

In some embodiments, using ultrasonic waves to power the implantable device can be advantageous over other power approaches because biological tissues have significantly lower absorption rates of ultrasonic waves than other types of waves such as radio frequency (RF) waves. This property of ultrasonic waves can allow the device to be implantable at greater depths in the subject as well as to reduce tissue heating due to energy absorbed by the tissue.

Even with these advantages, however, ultrasonic waves traversing biological tissue can still pose health hazards if too much power is transmitted and causes dangerous temperature increases in the exposed area of the patient's body. On the other hand, a host of factors such as the implanted depth, an orientation of an ultrasonic transducer of the implantable device, or intervening biological material (e.g., a rib bone or an organ) between the implantable device and an ultrasonic wave source can result in insufficient or inconsistent energy received at the implantable device to power its operations. Accordingly, there is a further need for systems, methods, and techniques that provide power controls for implantable devices powered using ultrasonic waves to enable safe operations and consistent power.

In some embodiments, to address the needs noted above, a device implantable in a subject includes: an ultrasonic transducer configured to receive powering ultrasonic waves from an interrogator and convert the powering ultrasonic waves into an electrical signal to power the implantable device, wherein the powering ultrasonic waves have a wave power; and a controller circuit configured to generate information that indicates whether more power or less power should be transmitted to the implantable device, and the ultrasonic transducer is further configured to transmit the information to the interrogator. As will be further described below, in some embodiments, the interrogator can be configured to receive the information and adjust the wave power of transmitted powering ultrasonic waves based on the information such that sufficient power can be provided to the implantable device without incurring safety risks.

In some embodiments, the device includes a power monitoring circuit configured to determine an available power at the implantable device and to determine a power consumed by the implantable device.

In some embodiments, the information includes a request for either more or less power from the interrogator. In some embodiments, the request is generated based on the available power at the implantable device and the power consumed by the implantable device.

In some embodiments, to transmit the information, the ultrasonic transducer is configured to: receive communication ultrasonic waves from the interrogator; and emit an ultrasonic backscatter of the communication ultrasonic waves, wherein the backscattered communication ultrasonic waves encodes the information.

In some embodiments, to emit the ultrasonic backscatter of the communication ultrasonic waves, the ultrasonic transducer is configured to: generate an electrical signal based on the communication ultrasonic waves; and modulate the generated electrical signal based on the information to encode the information into the ultrasonic backscatter.

In some embodiments, the ultrasonic transducer is configured to: receive second powering ultrasonic waves from the interrogator that is configured to generate the second powering ultrasonic waves to have a second wave power based on the information.

In some embodiments, the powering ultrasonic waves include a pulse width modulated (PWM) signal. In some embodiments, the interrogator is configured to adjust an instantaneous intensity value or a pulse width of the PWM signal based on the information. In some embodiments, the interrogator is configured to adjust the instantaneous intensity value and the pulse width of the PWM signal based on the information.

In some embodiments, the device includes: a voltage sensor configured to determine a maximum voltage of the ultrasonic transducer, and the power monitoring circuit is configured to determine the available power based on the maximum voltage.

In some embodiments, the device includes: a power conveyor circuit configured to charge an energy storage device based on the electrical signal, and the power monitoring circuit is configured to determine the available power based on energy stored at the energy storage device. In some embodiments, the power monitoring circuit is configured to determine the available power based on a rate of change of the energy stored at the energy storage device.

In some embodiments, the electrical signal generates a first voltage, the controller circuit is configured to control one or more switches to control a plurality of capacitors configured to convert the first voltage into a second voltage to power the implantable device, and the power monitoring circuit is configured to determine the available power based on a switching frequency of at least one of the one or more switches.

In some embodiments, the power monitoring circuit is configured to determine the consumed power of the implantable device based on an operating mode of the implantable device. In some embodiments, the operating mode includes nerve stimulation, neural-activity recording, or measurement or detection of a physiological condition. In some embodiments, the physiological condition includes temperature, pH, pressure, heart rate, strain, oxygen tension, a presence of an analyte, or an amount of the analyte.

In some embodiments, the consumed power is consumed by a load circuit of the implantable device, and the power monitoring circuit is configured to: detect a current value of an electrical current driving the load circuit; and determine the consumed power based on the detected current value. In some embodiments, the load circuit is configured to perform the operating mode.

In some embodiments, the power monitoring circuit is configured to determine a supply power provided by the electrical signal, and the electrical signal generates a first voltage at a first node. In some embodiments, the controller circuit is configured to determine if the supply power is greater than the consumed power. In some embodiments, the device includes: a power conveyer circuit configured to: receive the first voltage at the first voltage node based on the electrical signal; and convert the first voltage into a second voltage to power the implantable device, wherein the consumed power is associated with the second voltage.

In some embodiments, the device includes a voltage sensor configured to determine a maximum voltage of the ultrasonic transducer, and the power monitoring circuit is configured to determine the supply power based on the maximum voltage.

In some embodiments, the controller circuit is configured to: in response to determining that the supply power exceeds the consumed power, control the power conveyor circuit to charge an energy storage device based on the first voltage node, wherein charging the energy storage device reduces the first voltage.

In some embodiments, the controller circuit is configured to determine whether the energy storage device is fully charged.

In some embodiments, the controller circuit is configured to: in response to determining that the supply power exceeds the consumed power and that the energy storage device is fully charged, control the ultrasonic transducer to transmit to the interrogator the information including an indication that the implantable device is being over powered. In some embodiments, the information including the indication is configured to be receivable by the interrogator and causes the interrogator to generate second powering ultrasonic waves that have a second wave power that is less than the wave power of the powering ultrasonic waves.

In some embodiments, the controller circuit is configured to: determine if the first voltage exceeds a predefined voltage level; and in response to determining that the first voltage exceeds the predefined voltage level and that the energy storage device is fully charged, open one or more switches configured to generate the electrical signal from the powering ultrasonic waves to reduce the supply power.

In some embodiments, the controller circuit is configured to: in response to determining that the supply power is less than the consumed power, control the power conveyor circuit to discharge the energy storage device through the first voltage node, wherein discharging the energy storage device increases the first voltage.

In some embodiments, the controller circuit is configured to: in response to determining that the supply power is less than the consumed power, control the ultrasonic transducer to transmit to the interrogator the information including an indication that the implantable device is being under powered. In some embodiments, the information including the indication is configured to be receivable by the interrogator and causes the interrogator to generate second powering ultrasonic waves having a second wave power greater than the wave power of the powering ultrasonic waves.

In some embodiments, an interrogator device includes: an ultrasonic transducer configured to: transmit first powering ultrasonic waves to an implantable device, the first powering ultrasonic waves having a first wave power; receive communication ultrasonic waves from the implantable device, wherein the communication ultrasonic waves includes information indicating whether more power or less power should be transmitted to the implantable device; and transmit second powering ultrasonic waves to the implantable device, wherein the second powering ultrasonic waves have a second power based on the information.

In some embodiments, the interrogator device includes a controller configured to: extract the information from the communication ultrasonic waves; and control the ultrasonic transducer to transmit the second powering ultrasonic waves having the second power.

In some embodiments, the communication ultrasonic waves include an ultrasonic backscatter of previously-transmitted communication ultrasonic waves.

In some embodiments, the second powering ultrasonic waves include a PWM signal. In some embodiments, the ultrasonic transducer is configured to control an instantaneous intensity value or a pulse width of the PWM signal based on the information to cause the second powering ultrasonic waves to have the second wave power.

In some embodiments, a method of controlling power provided to a device implantable in a subject is implemented at the implantable device and includes: receiving powering ultrasonic waves from an interrogator, the powering ultrasonic waves having a wave power; converting energy from the powering ultrasonic waves into an electrical signal to power the implantable device; and transmitting to the interrogator information that indicates whether more power or less power should be transmitted to the implantable device.

Further described herein are various method embodiments for controlling power provided by an interrogator, according to any of the aforementioned embodiments, to an implantable device, according to any of the aforementioned embodiments.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the drawings.

DETAILED DESCRIPTION

Described herein are systems and methods for controlling power provided to a device implantable within a subject and powered using ultrasonic waves. As discussed above, these power controls may enable the implantable device to be operated safely and to be provided with consistent power. Therefore, the implantable device powered using ultrasonic waves can retain the advantages provided by ultrasonic waves such as enabling a smaller form factor and greater implantable depths without incurring potential disadvantages associated with the use of ultrasonic waves. In some embodiments, such an implantable device includes an ultrasonic transducer configured to receive powering ultrasonic waves having a wave power from an interrogator and convert the powering ultrasonic waves into an electrical signal to power the implantable device. The implantable device can include a controller circuit configured to generate information that indicates whether more power or less power should be transmitted to the implantable device. In some embodiments, the ultrasonic transducer can be further configured to transmit the information to the interrogator. In some embodiments, the interrogator can be configured to receive the information and adjust the wave power of the transmitted powering ultrasonic waves based on the information.

Figure 1:
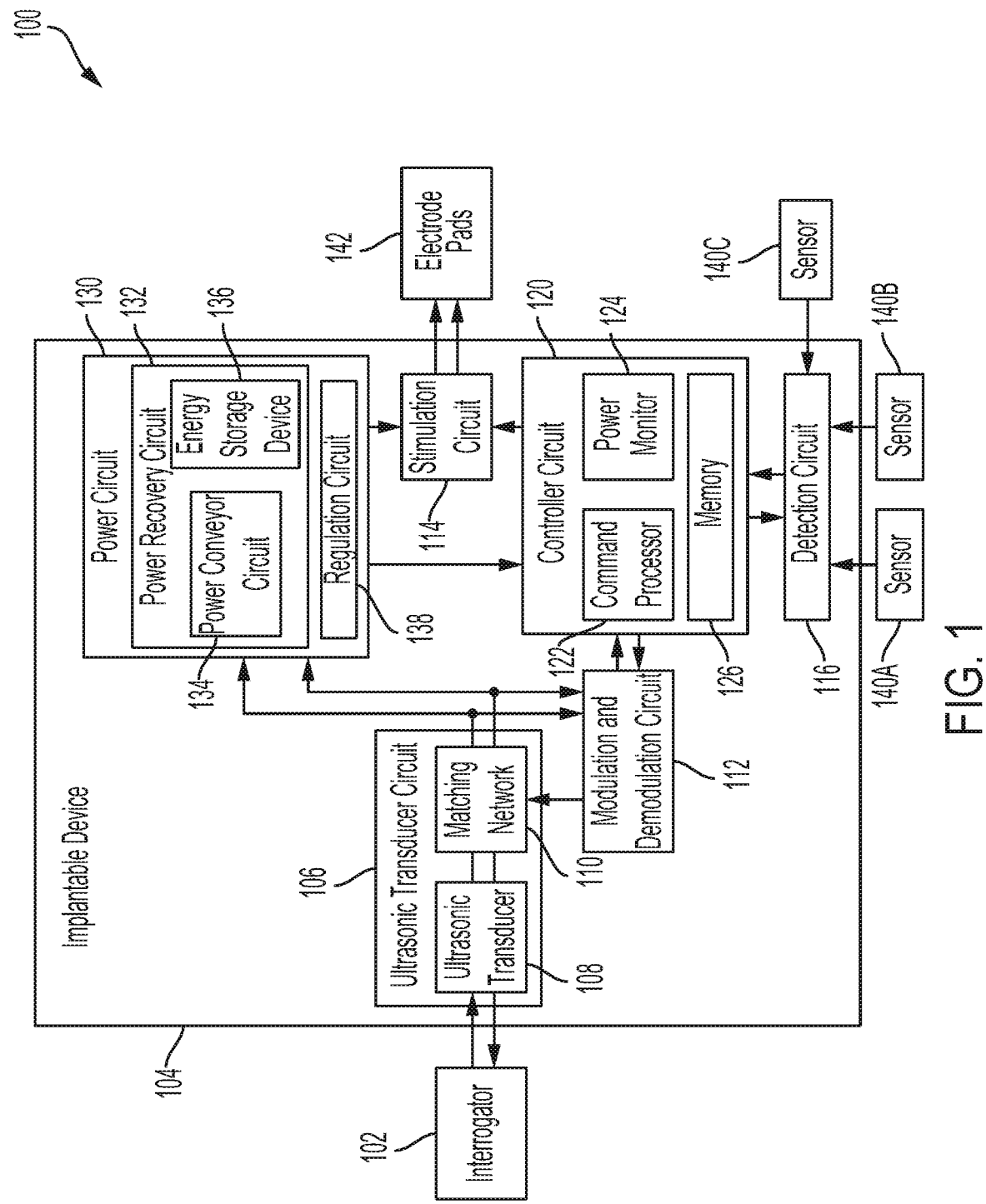
FIG. 1 illustrates a system including an implantable device powered using ultrasonic waves, according to some embodiments.

FIG. 1 illustrates a system 100 including an implantable device 104 powered using ultrasonic waves, according to some embodiments. In some embodiments, implantable device 104 can be wirelessly powered by ultrasonic waves transmitted from interrogator 102, as will be further described below with respect to FIG. 2. In some embodiments, implantable device 104 can be configured to wirelessly communicate with interrogator 102 through ultrasonic communication. In some embodiments, implantable device 104 can be implanted within a subject such as a patient and interrogator 102 can be a separate device that is external to (i.e., non-implanted) or fully-implanted in the subject. In some embodiments, power provided by interrogator 102 can be controlled based on bidirectional communications between interrogator 102 and implantable device 104. In some embodiment, interrogator 102 and implantable device 104 can be configured to communicate with each other using ultrasonic waves.

In some embodiments, to enable implantable device 104 to be powered using ultrasonic waves, implantable device 104 can include the following device components: an ultrasonic transducer circuit 106, a modulation and demodulation circuit 112, a stimulation circuit 114, a detection circuit 116, a controller circuit 120, and a power circuit 130. In some embodiments, one or more of these device components can be implemented as a digital circuit, an analog circuit, or a mixed-signal integrated circuit depending on their operations. For example, controller circuit 120 may include a microprocessor, a finite state machine (FSM), a field programmable gate array (FPGA), or a microcontroller.

In some embodiments, ultrasonic transducer circuit 106 includes an ultrasonic transducer 108 coupled to a matching network 110. In some embodiments, ultrasonic transducer circuit 106 does not include matching network 110. In some embodiments, ultrasonic transducer 108 can be configured to receive ultrasonic waves from interrogator 102 and convert energy from the received ultrasonic waves into an electrical signal to power one or more device components of implantable device 104. In some embodiments, the electrical signal can be generated by ultrasonic transducer 108 because vibrations of ultrasonic transducer 108 caused by the received ultrasonic waves induce a voltage across the electric terminals of ultrasonic transducer 108, which causes an electrical current to flow.

In some embodiments, as described above, power from the received ultrasonic waves can be used by implantable device 104 to power its device components; accordingly, these ultrasonic waves are sometimes referred to herein as powering ultrasonic waves. In some embodiments, the received ultrasonic waves can encode information including instructions for operating the implantable device; accordingly, these ultrasonic waves are sometimes referred to herein as communication ultrasonic waves. In some embodiments, similar to how powering ultrasonic waves can be processed, the communication ultrasonic waves can be received by ultrasonic transducer 108 to generate an electrical signal having an electrical current that flows through ultrasonic transducer 108. In some embodiments, the generated electrical signal encodes the information in the electrical current. In some embodiments, the same ultrasonic waves can be configured to both power implantable device 104 and to encode information for transmitting to implantable device 104.

In some embodiments, ultrasonic transducer circuit 106 includes a plurality of ultrasonic transducers coupled to a plurality of corresponding matching networks. By including at least two ultrasonic transducers, implantable device 104 can be configured to be powered by electrical signals generated by the at least two ultrasonic transducers to more efficiently and consistently extract power provided by interrogator 102, according to some embodiments.

For example, as described above, a host of factors such as an orientation of ultrasonic transducer or intervening biological material between ultrasonic transducer 108 and an ultrasonic wave source interrogator 102 may significantly reduce the power receivable at ultrasonic transducer 108. By adding one or more additional ultrasonic transducers, reduced power receivable at a single ultrasonic transducer (e.g., ultrasonic transducer 108) may be less likely to negatively impact operations of implantable device 104. In some embodiments, one or more of these ultrasonic transducers can be a micro machined ultrasonic transducer, such as a capacitive micro-machined ultrasonic transducer (CMUT) or a piezoelectric micro-machined ultrasonic transducer (PMUT), or can be a bulk piezoelectric transducer. Additionally implementations of ultrasonic transducer 108 are described below with respect to FIG. 5.

In some embodiments, matching network 110 can be an electronic circuit configured to select an impedance match between the electrical impedance of ultrasonic transducer 108 and the electrical impedance of implantable device 104 (e.g., power circuit 130) to reduce signal reflection. In some embodiments, matching network 110 can be implemented in various configurations of one or more circuit elements such as inductors, capacitors, resistors, diodes, transistors, or any combination thereof. For example, matching network 110 may be implemented as a plurality of capacitors connected in parallel and coupled to a plurality of corresponding switches. By controlling which of the switches open or close, matching network 110 may control how the plurality of capacitors is charged to select the impedance. In some embodiments, matching network 110 can be configured to enable the electrical signal generated by ultrasonic transducer 108 to bypass the plurality of capacitors via a separate wire controlled by a switch.

In some embodiments, to enable implantable device 104 to be powered using ultrasonic waves, power circuit 130 can include a power recovery circuit 132 electrically coupled to a regulation circuit 138. In some embodiments, power recovery circuit 132 can be configured to receive and process the electrical signal generated by ultrasonic transducer circuit 106. In some embodiments, power recovery circuit 132 can include a rectifying circuit (e.g., an active rectifier) to convert the electrical signal in an AC form to a DC form where the converted electrical signal may be associated with a first voltage (i.e., the supply voltage of the received ultrasonic waves).

In some embodiments, due to health hazards in propagating high-powered waves through biological tissue of the subject, government regulations may limit the amount of power (e.g., 720 mW/cm$^2$) provided by ultrasonic waves transmitted by interrogator 102. Therefore, the first voltage derived from the received ultrasonic waves may not be high enough to operate the electronic components of implantable device 104. For example, transistors used in complementary metal-oxide-semiconductor (CMOS) technology may require a minimum of about 2 Volts to operate the transistors.

In some embodiments, to provide a higher first voltage to operate the electronic components implantable device 102, the powering ultrasonic waves can be transmitted as a pulse width modulated (PWM) signal. In some embodiments, by transmitting the powering ultrasonic waves as the PWM signal, interrogator 102 can be configured to provide short, high intensity pulses such that the average intensity stays within the regulation limits and to provide higher instantaneous power to generate a higher first voltage. In some embodiments, the interrogator can be configured to control an instantaneous intensity and/or a pulse width (e.g., example ultrasonic wave settings) of the PWM signal to control the power provided by the powering ultrasonic waves.

In some embodiments, to enable implantable device 104 to be powered by these ultrasonic waves, power conveyor circuit 134 can include a charge pump configured to convert the first voltage to a second voltage greater than the first voltage. In some embodiments, the charge pump can include a plurality of coupled capacitors controlled by one or more switches to generate the second voltage. In some embodiments, the charge pump can achieve conversion gains of at least 1×, 2×, 3×, or 4×. In some embodiments, the magnitude of the second voltage can be controlled based on a switching frequency of the one or more switches.

As discussed the above, power provided by the received ultrasonic waves can be inconsistent due to a host of factors including, for example, an implant depth of implantable device 104 or intervening biological material between ultrasonic transducer 108 and the ultrasonic wave source, e.g., interrogator 102. Accordingly, in some embodiments, to provide more consistent power to implantable device 104, power recovery circuit 132 can include an energy storage device 136 coupled to power conveyor circuit 134. In some embodiments, the energy storage device includes a battery or a storage capacitor. In some embodiments, to retain the small form factor of implantable device 104, the energy storage device can be configured as a storage capacitor.

In some embodiments, the storage capacitor can have a capacitance that is at least 0.1 µF, at least 0.25 µF, at least 0.5 µF, at least 1 µF, at least 2 µF, at least 4 µF, or at least 8. In some embodiments, the storage capacitor can have a capacitance that is less than 10 µF, less than 8 µF, less than 4 µF, less than 2 µF, less than 1 µF, less than 0.5 µF, or less than 0.25 µF. For example, the storage capacitor may have a capacitance in the range of 0.1-10 µF such as in the range of 0.5-2 µF. In some embodiments, the storage capacitor can have a capacitance that is about 1 µF.

In some embodiments, energy storage device 136 can be configured to operate in at least two power modes to enable implantable device 104 to more efficiently utilize power of received ultrasonic waves and to provide more consistent power. In some embodiments, the power modes include a charging mode in which a portion of power of the received ultrasonic waves can be conveyed to energy storage device 136 capable of storing the energy. In some embodiments, power conveyor circuit 134 can be configured to charge energy storage device 136 based on the generated first voltage. In some embodiments, the power modes include a discharging mode in which a portion of energy stored at energy storage device 136 is discharged to convey power from energy storage device 136 to provide additional power to other device components (e.g., stimulation circuit 114, detection circuit 116, or controller circuit 120, etc.) of implantable device 104. In some embodiments, the power flow to and from energy storage device 136 can be routed through power conveyor circuit 134.

In some embodiments, regulation circuit 138 can be configured to regulate the output voltage (e.g., the second voltage) generated by power conveyor circuit 134 to provide regulated voltages to one or more circuit loads of implantable device 104. In some embodiments, where power conveyor circuit 134 includes a charge pump, regulation circuit 138 can be configured to remove or reduce potential voltage ripples caused by operating switches of the charge pump. In some embodiments, regulation circuit 138 includes a DC voltage regulator (e.g., a low-dropout (LDO) regulator) to regulate a voltage supplied to digital circuit loads of implantable device 104. In some embodiments, regulation circuit 138 includes a DC voltage regulator (e.g., a low-dropout (LDO) regulator) to regulate a voltage supplied to digital circuit loads of implantable device 104. In some embodiments, regulation circuit 138 includes an AC voltage regulator (e.g., a low-dropout (LDO) regulator) to regulate a voltage supplied to analog circuit loads of implantable device 104.

In some embodiments, modulation and demodulation circuit 112 can include a demodulation circuit configured to demodulate the electrical signal generated by ultrasonic transducer circuit 106 to extract information encoded in the received ultrasonic waves. In some embodiments, the demodulation circuit can transmit the extracted information including an instruction to controller circuit 120 configured to control how implantable device 104 operates based on the instruction.

In some embodiments, to enable implantable device 104 to wireless communicate information with interrogator 102, modulation and demodulation circuit 112 can include a modulation circuit configured to encode the information using ultrasonic backscatter. This information is generated by implantable device 104 and, for ease of explanation, will sometimes be referred to as device information in the following descriptions.

In general, when implantable device 104 is embedded within a subject, the ultrasonic waves (including carrier waves) emitted by an ultrasonic transceiver of interrogator 102 will pass through biological tissue before being received by ultrasonic transducer circuit 106 of implantable device 104. As described above, the carrier waves cause mechanical vibrations on ultrasonic transducer 108 (e.g., a bulk piezoelectric transducer) to generate a voltage across ultrasonic transducer 108, which then imparts an electrical current to flow to the rest of implantable device 104. In some embodiments, the electrical current flowing through ultrasonic transducer 108 causes ultrasonic transducer circuit 106 to emit backscatter ultrasonic waves corresponding to the received ultrasonic waves.

In some embodiments, the modulation circuit can be configured to modulate the electrical current flowing through ultrasonic transducer 108 to encode the device information, which causes the resulting ultrasonic backscatter waves to also encode the device information. Accordingly, the ultrasonic backscatter emitted from implantable device 104 can encode the device information related to implantable device 104. In some embodiments, the modulation circuit can include one or more switches, such as an on/off switch or a field-effect transistor (FET). An example FET that may be used with some embodiments of implantable device 104 includes a metal-oxide-semiconductor field-effect transistor (MOSFET). In some embodiments, the modulation circuit can be configured to alter the impedance of an electrical current flowing through ultrasonic transducer 108, and variation in the flowing electrical current flowing encodes the information.

As will be further described below with respect to FIGS. 2 and 3, the ultrasonic backscatter can be received by interrogator 102 and deciphered to extract the device information encoded in the ultrasonic backscatter, according to some embodiments. In some embodiments, the ultrasonic backscatter can be received by an interrogator that may be the same or different than interrogator 102 that transmitted the ultrasonic waves received by ultrasonic transducer 108.

In some embodiments, detection circuit 116 can be configured to interface with one or more sensors 140A-C to measure or detect one or more physiological conditions of the subject. In some embodiments, detection circuit 116 can include a driver configured to provide current to the one or more sensors 140A-C and receive generated signals from the one or more sensors 140A-C. In some embodiments, a received signal can include information representative of a detected physiological condition or representative of a measured physiological condition. In some embodiments, detection circuit 116 can be configured to transmit the information to controller circuit 120.

In some embodiments, one or more of sensors 140A-C can be located inside implantable device 104 or coupled to the exterior of implantable device 104. In some embodiments, implantable device 104 includes at least two sensors 140A-C. In some embodiments, the one or more physiological conditions can include temperature, pH, pressure, heart rate, strain, oxygen tension, a presence of an analyte, or an amount of the analyte. For example, the analyte may be oxygen or glucose.

In some embodiments, sensors 140A-C can include an optical sensor. In some embodiments, the optical sensor comprises a light source and an optical detector. In some embodiments, the optical sensor detects blood pressure or a pulse. In some embodiments, the optical sensor comprises a matrix comprising a fluorophore or luminescent probe, and wherein fluorescence intensity or fluorescence lifetime of the fluorophore depends on the amount of the analyte. In some embodiments, the optical sensor is configured to perform near-infrared spectroscopy. In some embodiments, the optical sensor detects glucose.

In some embodiments, sensors 140A-C can include a potentiometric chemical sensor or an amperometric chemical sensor. In some embodiments, the sensor detects oxygen, pH, or glucose.

In some embodiments, sensors 140A-C can include a temperature sensor. In some embodiments, the temperature sensor is a thermistor, a thermocouple, or a proportional to absolute temperature (PTAT) circuit.

In some embodiments, sensors 140A-C can include a pressure sensor. In some embodiments, the pressure sensor is a microelectromechanical system (MEMS) sensor. In some embodiments, detection circuit 116 is configured to measure blood pressure or a pulse.

In some embodiments, sensors 140A-C can include a strain sensor.

In some embodiments, detection circuit 116 can be configured to interface with, for example, sensor 140C to detect an electrophysiological signal from a nerve or a targeted subset of nerve fibers within the nerve, as will be further explained below with respect to FIG. 5. In some embodiments, sensor 140C can include electrode pads, which may be the same or different from electrode pads 142 operated by stimulation circuit 114. In some embodiments, detection circuit 116 can be configured to record neural activity of a nerve or the targeted subset of nerve fibers based on the detected electrophysiological signal.

In some embodiments, one or more techniques such as computational modeling (e.g., finite element models), inverse source estimation, multipole (e.g., tripole) neural recording, velocity-selective recording, or beamforming can be implemented by detection circuit 116 (alone or in conjunction with controller circuit 120) to selectively target the subset of nerve fibers. See, for example, Taylor et al., *Multiple-electrode nerve cuffs for low-velocity and velocity selective neural recording*, Medical & Biological Engineering & Computing, vol. 42, pp. 634-643 (2004); and Wodlinger et al., *Localization and Recovery of Peripheral Neural Sources with Beamforming Algorithms*, IEEE Transactions on Neural Systems and Rehabilitation Engineering, vol. 17, no. 5, pp. 461-468 (2009).

In some embodiments, detection circuit 116 can be configured to operate the plurality of electrodes of sensor 140C for targeted detection of the electrophysiological signal. For example, sensor 140C may be a curved member that extends from implantable device 104, as further described below with respect to FIG. 5. In some embodiments, detection circuit 116 can analyze the electrophysiological signal detected by all or a subset of the electrode pads to determine the subset of nerve fibers within the nerve that are transmitting the electrophysiological signal. Certain nerves may transmit compound electrophysiological signal (or compound action potentials), which is the sum of the electrophysiological signals (or action potentials) simultaneously transmitted by two or more different subsets of nerve fibers. Based on the electrophysiological signal detected by the plurality of electrode pads, detection circuit 116 may be able to determine which subset of nerve fibers transmits which electrophysiological signal. In some embodiments, data received from interrogator 102 (such as temperature data, or data related to an analyte concentration or other physiological condition) is further used to determine which subset of nerve fibers transmits the electrophysiological signal.

For example, in some embodiments, detection circuit 116 may be configured to selectively detect an electrophysiological signal from a targeted subset of nerve fibers using velocity-selective recording, which may be combined with multipolar (e.g., tripolar) recording (which can include any number of tripoles within the plurality of electrodes on one or more curved members).

Beamforming can additionally or alternatively be used to detect the electrophysiological signals from the targeted subset of nerve fibers. A portion of or all of the electrode pads of one or more curved members can detect the electrophysiological signal from the nerve, and detection circuit 116 can determine the cross-sectional location of the transmitted signal within the nerve based on the differences in electrophysiological signal detected by a portion or all of the electrode pads of the one or more curved members.

In some embodiments, stimulation of one or more nerves at a location separate from the location of implantable device 104 can result in a modulation of the electrophysiological signal at the location of implantable device 104. The modulation of the electrophysiological signal detected at different subsets of nerve fibers within the nerve in electrical communication with the electrode pads (e.g., electrode pads 142) of implantable device 104 can be the result of stimulation in different distant nerves. For example, stimulation of the splenic nerve can result in modulation of an electrophysiological signal detected from first subset of nerve fibers within the vagus nerve, and stimulation of a renal nerve can result in modulation of an electrophysiological signal detected from a second subset of nerve fibers within the vagus nerve. Therefore, an implantable device positioned on the vagus nerve can detect an electrophysiological signal from the first subset of nerve fibers to monitor stimulation of the splenic nerve, and a second subset of nerve fibers to monitor stimulation of the renal nerve.

In some embodiments, stimulation circuit 114 can be configured to emit a targeted electrical pulse to a subset of nerve fibers within the nerve by selectively activating one or more electrode pads 142 connected to the subset of nerve fibers. In some embodiments, implantable device 104 can include one or more curved members that electrically connect stimulation circuit 114 to electrode pads 142, as will be further described below with respect to FIG. 5.

In some embodiments, stimulation circuit 114 can be controlled by controller circuit 120 to operate electrode pads 142 or to selectively activate electrode pads 142. Selective activation can include, for example, activating a portion of electrode pads within the plurality of electrode pads 142 of one or more curved members and/or differentially activating all or a portion of the electrode pads within the plurality of electrode pads 142 of the one or more curved members. The plurality of electrodes can therefore be operated to steer the electrical pulse emitted by the plurality of electrode pads 142 to the target subset of nerve fibers. Techniques such as electrical field interference or multipolar stimulation (e.g., tripolar stimulation) can be used to target the electrical pulse to the subset of nerve fibers within the nerve, according to some embodiments. See, for example, Grossman, et al., *Noninvasive Deep Brain Stimulation via Temporally Interfering Electrical Fields*, Cell, vol. 169, pp. 1029-1041 (2017). Electrode pads 142 within one or more curved members can be selectively activated by controller circuit 120 to target the emitted electrical pulse to the subset of nerve fibers.

The subset of nerve fibers targeted by the emitted electrical pulse can be the same or different as the subset of nerve fibers from which the electrophysiological signal is detected by detection circuit 116. The one or more curved member configured to emit the targeted electrical pulse can be the same or different as the one or more curved members on implantable device 104 configured to detect the electrophysiological signal. The emitted targeted electrical pulse can stimulate the nerve at the position of implantable device 104. The subset of nerve fibers targeted by the electrical pulse can be the same or a different subset of nerve fibers for which the electrophysiological signal is selectively detected.

The subset of nerve fibers targeted by the electrical pulse emitted by implantable device 104 can be, for example, one or more (e.g., 2, 3, 4, or more) fascicles, or a portion of one or more (e.g., 2, 3, 4, or more) fascicles within the nerve. In some embodiments, the subset of nerve fibers comprises or consists of afferent nerve fibers within the nerve, or a subset of afferent nerve fibers within the nerve. In some embodiments, the subset of nerve fibers comprises or consists of efferent nerve fibers within the nerve, or a subset of efferent nerve fibers within the nerve. In some embodiments, the subset of nerve fibers comprises or consists of efferent nerve fibers within two or more fascicles within the nerve or afferent nerve fibers within two or more fascicles within the nerve.

Targeted stimulation of a subset of nerve fibers by emitting a targeted electrical pulse to the subset of nerve fibers can result in stimulation of a nerve at a location distant from the position of the nerve. The distant nerve stimulated by implantable device 104 depends on the subset of nerves at the position of implantable device 104 targeted by the electrical pulse emitted by the device. In some embodiments, implantable device 104 is positioned at a first nerve locus and is configured to stimulate a second nerve locus by emitting a targeted electrical pulse to a subset of nerve fibers within the first nerve locus that is associated with the second nerve locus. In some embodiments, the first nerve locus and the second nerve locus are separated by one or more nerve branch points or one or more synapses. In some embodiments, the second nerve locus is proximal to the brain relative to the first nerve locus, and in some embodiment the second nerve locus is distal from the brain relative to the first nerve locus. In some embodiments, the targeted subset of nerve fibers comprises or consists of afferent nerve fibers. In some embodiments, the targeted subset of nerve fibers comprises or consists of efferent nerve fibers.

In some embodiments, controller circuit 120 includes a command processor 122, a power monitor 124, and a memory 126. In some embodiments, memory 126 includes a non-transitory storage memory such as register memory, a processor cache, or Random Access Memory (RAM). In some embodiments, controller circuit 120 can be a digital circuit, an analog circuit, or a mixed-signal integrated circuit. Examples of controller circuit 120 may include a microprocessor, a finite state machine (FSM), a field programmable gate array (FPGA), and a microcontroller.

In some embodiments, command processor 122 can be configured to receive an instruction from the information encoded in received ultrasonic waves and extracted by modulation and demodulation circuit 112. In some embodiments, command processor 122 can store the received instruction in memory 126 such as an instruction register. In some embodiments, command processor 122 can be configured to control implantable device 104 to enter an operating mode based on the instruction and stored logic. For example, command processor 122 may be implanted as a FSM that controls the operating mode of implantable device 104 based on a current operating mode and one or more detected inputs such as one or more received instructions, one or more sensor values, or a combination thereof.

Information encoded in the ultrasonic waves emitted by the interrogator and received by the closed-loop implantable device can include, for example, instructions for starting or stopping neuromodulation, one or more calibration instructions, one or more updates to the operation software, and/or or one or more templates (such as template electrophysiological signals, one or more template electrophysiological signals, and/or one or more template stimulation signals). In some embodiments, command processor 122 can be configured to process and store the received instructions in memory 126. In some embodiments, command processor 122 can enter an operating mode from a plurality of operating modes based on one or more received instructions. In some embodiments, the plurality of operating modes can include a mode to stimulate a nerve, a mode to record neural activity, or a mode to determine one or more physiological conditions. For example, if the instruction indicates that implantable device 104 should enter the neural stimulation mode, controller circuit 120 may be configured to control stimulation circuit 114 to stimulate specific nerve fibers or portions of the nerve.

In some embodiments, when command processor 122 controls implantable device 104 to enter the neural activity recording mode or a mode to determine one or more physiological conditions, command processor 122 may control detection circuit 116 to retrieve the device information (e.g., neural record or detected/measured physiological condition). In some embodiments, upon retrieving the device information, command processor 122 can be configured to control modulation and demodulation circuit 112 to encode the device information in an ultrasonic backscatter, as described above.

In some embodiments, to provide power controls to implantable device 104, power monitor 124 can be configured to monitor an available power and a power consumption of implantable device 104, as will be further described below with respect to FIG. 3. In some embodiments, the available power can include a supply power provided by the ultrasonic waves received at ultrasonic transducer 108 and include an accessible power stored on implantable device 104. For example, the accessible power may include power accessible from energy storage device 136 storing excess energy. In some embodiments, power monitor 124 can determine the power consumption based on an output voltage generated by power conveyor circuit 134, as will be further described below with respect to FIG. 3.

In some embodiments, command processor 122 can be configured to generate information indicating whether more power or less power should be transmitted to implantable device 104 based on the available power and the consumed power monitored by power monitor 124. In some embodiments, controller circuit 120 can be configured to implement method 400, as described below with respect to FIG. 4, to generate the information. In some embodiments, controller circuit 120 can be configured to control modulation and demodulation circuit 112 to encode the generated information in an ultrasonic backscatter, as will be further described below with respect to FIG. 3.

Figure 2:
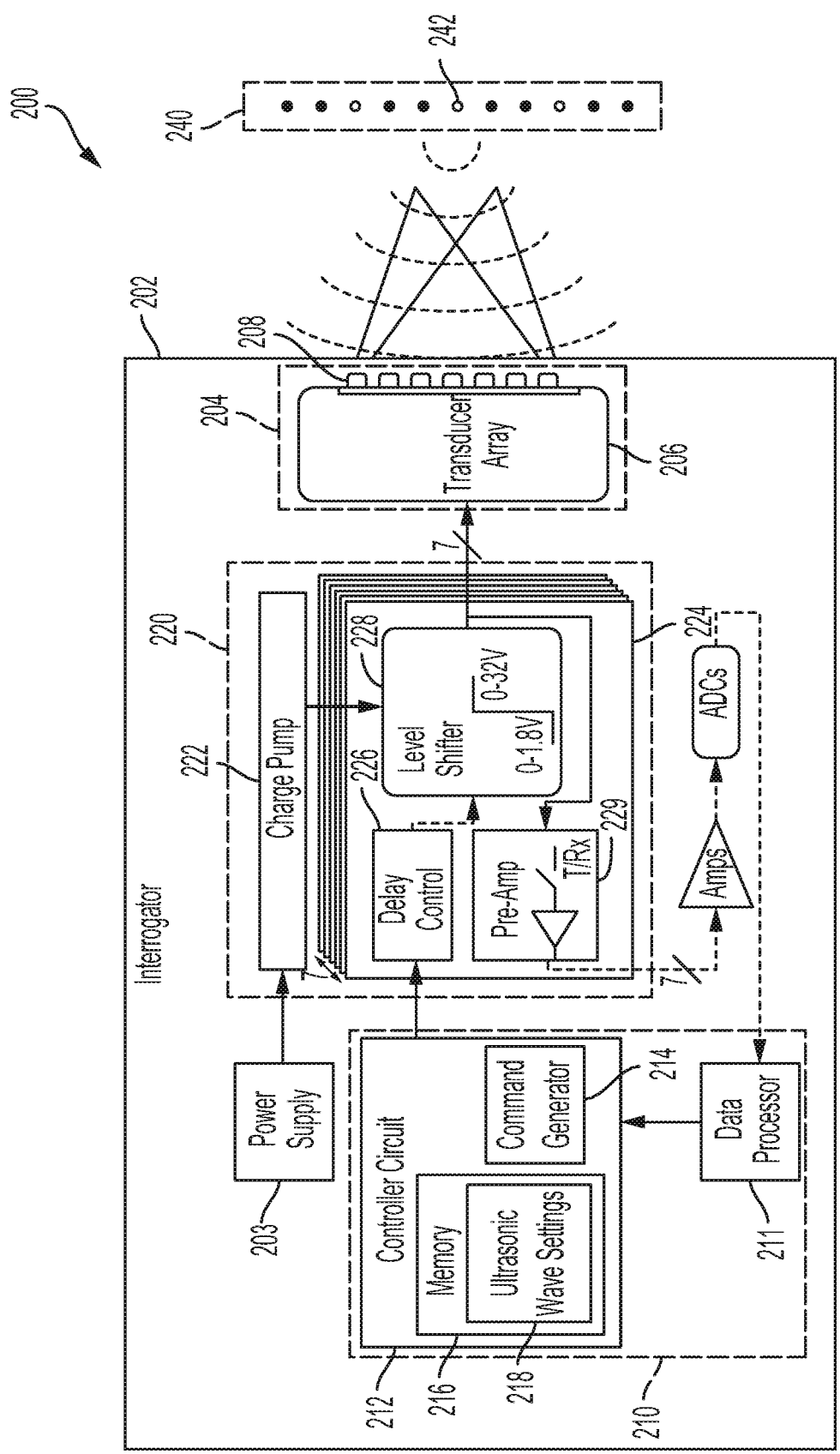
FIG. 2 illustrates a system including an interrogator configured to power one or more implantable devices using ultrasonic waves, according to some embodiments.

FIG. 2 illustrates a system 200 including an interrogator 202 configured to power one or more implantable devices 240 using ultrasonic waves, according to some embodiments. In some embodiments, interrogator 202 can be an example of interrogator 102 or interrogator 302 as described with respect to FIGS. 1 and 3, respectively. In some embodiments, interrogator 202 can be configured to perform one or more of the steps of method 400 of FIG. 4, as described below.

In some embodiments, interrogator 202 includes a power supply 203, a computational circuit 210, a signal-generation circuit 220, and an ultrasonic transducer circuit 204. As shown, power supply 203 can be configured to power computational circuit 210 and signal-generation circuit 220. In some embodiments, power supply 203 can provide 1.8V, although any suitable voltage can be used. For example, power supply 203 may include one or more batteries to supply the 1.8V.

In some embodiments, signal-generation circuit 220 includes a charge pump 222 configured to power one or more channels 224. In some embodiments, charge pump 222 can be configured to increase the voltage provided by power supply 203. For example, charge pump 222 may increase the 1.8V supplied by power supply 203 to 32V.

In some embodiments, each channel 224 is coupled to and controls an operation of a corresponding ultrasonic transducer 208 of transducer circuit 204. In some embodiments, ultrasonic transducer 208 connected to channel 224 can be configured only to receive or only to transmit ultrasonic waves, in which case switch 229 can be optionally omitted from channel 224. In some embodiments, each channel 224 can include the following electronic components: a delay control 226, a level shifter 228, and a switch 229.

In some embodiments, delay control 226 can be configured to control the waveforms and/or signals of ultrasonic waves transmitted by ultrasonic transducer 208. In some embodiments, delay control 226 can control, for example, a phase shift, a time delay, a pulse frequency, a wave shape (including amplitude and wavelength), or a combination thereof based on commands from controller circuit 212 to generate the transmit waveform. In some embodiments, the data representing the wave shape and frequency for each channel can be stored in a 'wave table' stored in delay control 226 or in memory 216. This may allow the transmit waveform on each channel 224 to be different.

In some embodiments, delay control 226 can be connected to a level shifter that is configured to shift input pulses from delay control 226 to a higher voltage used by ultrasonic transducer 208 to transmit the ultrasonic waves. In some embodiments, delay control 226 and level shifter 228 can be configured to be used to stream data to the actual transmit signals to transducer array 206. In some embodiments, the transmit waveform for each channel 224 can be produced directly by a high-speed serial output of a microcontroller or other digital system and sent to the transducer element (e.g., ultrasonic transducer 208) through level shifter 228 or a high-voltage amplifier.

In some embodiments, switch 229 of channel 224 can configure a corresponding ultrasonic transducer 208 to receive ultrasonic waves such as an ultrasonic backscatter. In some embodiments, the received ultrasonic waves are converted to an electrical current by ultrasonic transducer 208 (set in a receiving mode) and transmitted to data processor 211 to process data captured in the received ultrasonic waves. In some embodiments, an amplifier, an analog-todigital converter (ADC), a variable-gain-amplifier, or a time-gain-controlled variable-gain-amplifier which compensates for tissue loss, and/or a band pass filter can be included to process the received ultrasonic waves.

In some embodiments, channel 224 described above does not include a T/Rx switch 229, but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, transducer array 206 includes more transducer elements (e.g., ultrasonic transducer 208) than processing channels 224, and interrogator 202 can be configured to include a multiplexer to select different sets of transmitting elements for each pulse. For example, 64 transmit/receive channels may be connected via a 3:1 multiplexer to 192 physical transducer elements—with only 64 transducer elements active on a given pulse.

In some embodiments, computational circuit 210 can be a digital circuit, an analog circuit, or a mixed-signal integrated circuit. Examples of computational circuit 210 may include a microprocessor, a finite state machine (FSM), a field programmable gate array (FPGA), and a microcontroller. In some embodiments, interrogator 202 can include a volatile memory, which can be accessed by computational circuit 210.

In some embodiments, computational circuit 210 includes controller circuit 212 and data processor 211. In some embodiments, controller circuit 212 includes command generator 214 and memory 216 storing ultrasonic wave settings 218.

In some embodiments, command generator 214 can be configured to generate instructions to control operation of delay control 226. In some embodiments, based on device information received from an implantable device such as implantable device 242, command generator 214 can be configured to set or select ultrasonic wave settings to control an output power of transmitted ultrasound waves, as will be further described below with respect to FIG. 3. For example, received device information may indicate that more power should be transmitted to implantable device 242. In this example, command generator 214 may select ultrasonic wave settings 218, such as a higher pulse width or a higher instantaneous intensity, of the waveform to increase power of ultrasonic waves transmitted by ultrasonic transducer circuit 204.

In some embodiments, transducer circuit 204 includes one or more ultrasonic transducers 208 configured to transmit ultrasonic waves to power implantable devices 240 such as implantable device 242. In some embodiments, as shown in FIG. 2, transducer circuit 204 includes transducer array 206 having a plurality of ultrasonic transducers 208. In some embodiments, transducer array 206 includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more ultrasonic transducers. In some embodiments, transducer array 206 includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer ultrasonic transducers. Transducer array 206 may be, for example, a chip comprising 50 or more ultrasonic transducer pixels.

As shown in FIG. 2, transducer circuit 204 includes a single transducer array 206; transducer circuit 204, however, can include 1 or more, 2 or more, or 3 or more separate transducer arrays, according to some embodiments. In some embodiments, transducer circuit 204 includes 10 or fewer transducer arrays (such as 9, 8, 7, 6, 5, 4, 3, 2, or 1 transducer arrays). In some embodiments, the separate transducer arrays can be placed at different points of a subject, and can communicate to the same or different implantable devices 240. In some embodiments, the transducer arrays can be located on opposite sides of an implantable device such as implantable device 242.

In some embodiments, the specific design of transducer array 206 of interrogator 202 depends on the desired penetration depth, aperture size, and size of the individual ultrasonic transducers 208 within transducer array 206. The Rayleigh distance, R, of the transducer array 206 is computed as:

$$R = \frac{D^2 - \lambda^2}{4\lambda} \approx \frac{D^2}{4\lambda}, D^2 \gg \lambda^2$$

where D is the size of the aperture and $\lambda$ is the wavelength of ultrasound in the propagation medium (i.e., the tissue). As understood in the art, the Rayleigh distance is the distance at which the beam radiated by transducer array 206 is fully formed. That is, the pressure filed converges to a natural focus at the Rayleigh distance to maximize the received power. Therefore, in some embodiments, implantable devices 240 can be approximately the same distance from transducer array 206 as the Rayleigh distance.

The individual ultrasonic transducers 208 in transducer array 206 can be modulated to control the Raleigh distance and the position of the beam of ultrasonic waves emitted by transducer array 206 through a process of beamforming or beam steering. Techniques such as linearly constrained minimum variance (LCMV) beamforming can be used to communicate a plurality of implantable devices 240 (e.g., implantable device 242) with an external ultrasonic transceiver. See, for example, Bertrand et al., *Beamforming Approaches for Untethered. Ultrasonic Neural Dust Motes for Cortical Recording: a Simulation Study*, IEEE EMBC (August 2014). In some embodiments, beam steering is performed by adjusting the power or phase of the ultrasonic waves emitted by ultrasonic transducers 208 in transducer array 206.

In some embodiments, interrogator 202 (e.g., computational circuit 210) includes one or more of instructions for beam steering ultrasonic waves using one or more ultrasonic transducers 208, instructions for determining the relative location of one or more implantable devices 240, instructions for monitoring the relative movement of one or more implantable devices 240, instructions for recording the relative movement of one or more implantable devices 240, and instructions for deconvoluting backscatter from a plurality of implantable devices 240.

In some embodiments, interrogator 202 includes a user interface (not shown) that allows a user (e.g., a physician or a patient) to control the operations of interrogator 202 to power implantable devices 240 or to communicate with implantable devices 240. In some embodiments, the user interface can include an input device that provides input, such as a touch screen or monitor, keyboard, mouse, or voice-recognition device to interrogator 202. In some embodiments, the user interface can include an output device such as any suitable device that provides output, such as a touch screen, monitor, printer, disk drive, or speaker.

In some embodiments, interrogator 202 can be controlled using a separate computer system (not shown), such as a mobile device (e.g., a smartphone or a tablet). The computer system can wirelessly communicate to interrogator 202, for example through a network connection, a radiofrequency (RF) connection, or Bluetooth. The computer system may, for example, turn on or off interrogator 202 or analyze information encoded in ultrasonic waves received by interrogator 202.

In some embodiments, interrogator 202 communicates with a plurality of implantable devices 240. This can be performed, for example, using multiple-input, multiple output (MIMO) system theory. For example, communication between interrogator 202 and the plurality of implantable devices 240 may be performed using time division multiplexing, spatial multiplexing, or frequency multiplexing. Interrogator 202 can receive a combined ultrasonic backscatter from the plurality of the implantable devices 240, which can be deconvoluted, thereby extracting information from each implantable device 242. In some embodiments, interrogator 202 can be configured to focus the ultrasonic waves transmitted from transducer array 206 to a particular implantable device through beam steering. For example, interrogator 202 may focus the transmitted ultrasonic waves to a first implantable device (e.g., implantable device 242), receives backscatter from the first implantable device, focuses transmitted ultrasonic waves to a second implantable device, and receives backscatter from the second implantable device. In some embodiments, interrogator 202 transmits ultrasonic waves to a plurality of implantable devices 240, and then receives ultrasonic backscatter from the plurality of implantable devices 240.

In some embodiments, interrogator 202 or one or more of ultrasonic transducers 208 are wearable. For example, interrogator 202 or one or more of ultrasonic transducers 208 may be fixed to the subject's body by a strap or adhesive. In another example, interrogator 202 can be a wand, which may be held by a user (such as a healthcare professional). In some embodiments, interrogator 202 can be held to the body via suture, simple surface tension, a clothing-based fixation device such as a cloth wrap, a sleeve, an elastic band, or by sub-cutaneous fixation. In some embodiments, one or more ultrasonic transducers 208 or transducer array 206 of interrogator 202 may be positioned separately from the rest of interrogator 202. For example, transducer array 206 may be fixed to the skin of a subject at a first location (such as proximal to one or more implanted devices), and the rest of interrogator 202 may be located at a second location, with a wire tethering ultrasonic transducer 208 or transducer array 206 to the rest of interrogator 202.

Figure 3:
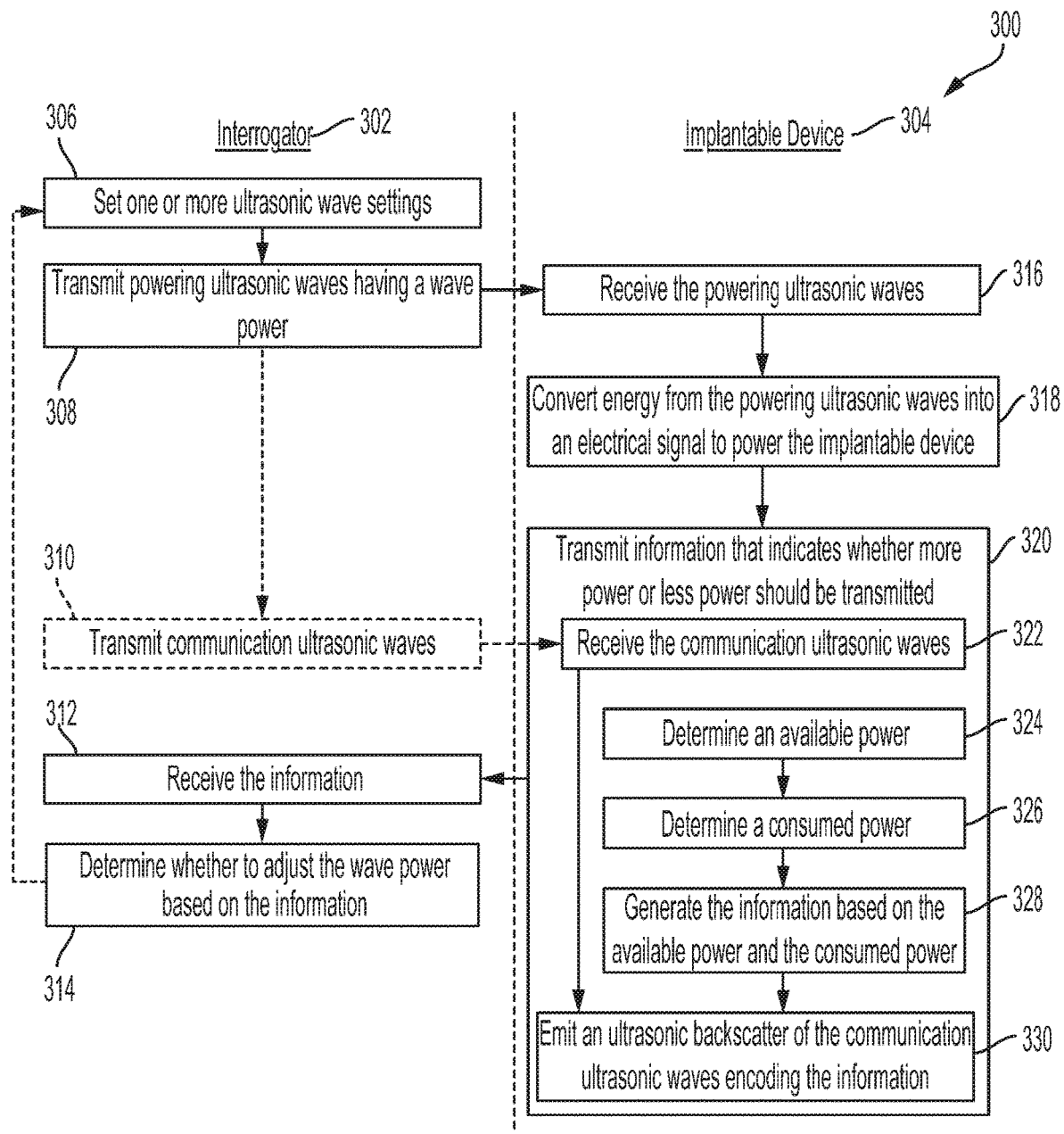
FIG. 3 illustrates a method for controlling power provided by an interrogator to an implantable device, according to some embodiments.

FIG. 3 illustrates a method 300 for controlling power provided by an interrogator 302 to an implantable device 304, according to some embodiments. In some embodiments, interrogator 302 and implantable device 304 may be examples of implantable device 104 of FIG. 1 and interrogator 202 of FIG. 2, respectively. Accordingly, for ease of explanation, various steps below may refer to the components of implantable device 104 or interrogator 202.

In step 306, interrogator 302 sets one or more ultrasonic wave settings (e.g., ultrasonic wave settings 218). In some embodiments, an ultrasonic wave setting includes a command to select a waveform from a plurality of stored waveforms. For example, the waveforms may be stored in a data table in a non-transitory memory (e.g., memory 216 or in delay control 226). In some embodiments, an ultrasonic wave setting includes a wave parameter of ultrasonic waves transmitted by interrogator 302. For example, the wave parameter may include a period, a frequency, an amplitude (i.e., intensity), a wavelength, a pulse duration, a pulse repetition rate, etc. In some embodiments, interrogator 302 sets a plurality of ultrasonic wave settings corresponding to a plurality of wave parameters.

In step 308, interrogator 302 transmits powering ultrasonic waves having a wave power. In some embodiments, interrogator 302 can be configured to generate the powering ultrasonic waves based on the one or more ultrasonic wave settings set in step 306. Therefore, the wave power may depend on the one or more ultrasonic wave settings.

In some embodiments, the transmitted powering ultrasonic waves can include a pulse width modulated (PWM) signal. In these embodiments, the one or more ultrasonic wave settings can include information associated with an instantaneous intensity value of the PWM signal, a pulse width of the PWM signal, or a combination thereof. By selecting or setting the one or more ultrasonic wave settings, interrogator 302 can be configured to adjust the wave power of transmitted powering ultrasonic waves.

In some embodiments, interrogator 302 can be configured to send separate ultrasonic waves to implantable device 304 to request information from implantable device 304 regarding whether more power or less power should be transmitted to implantable device 304. For example, in step 310, interrogator 302 transmits communication ultrasonic waves to implantable device 304. In some embodiments, the communication ultrasonic waves are separate from the powering ultrasonic waves of step 308 and may correspond to different ultrasonic wave settings than those of the powering ultrasonic waves. In some embodiments, a controller circuit (e.g., controller circuit 212) of interrogator 302 can be configured to determine the type of ultrasonic waves to transmit (e.g., powering ultrasonic waves or communication ultrasonic waves) based on user input received at interrogator 202 or based on information transmitted from implantable device 304.

In step 316, implantable device 304 receives the powering ultrasonic waves from interrogator 302 with the powering ultrasonic waves having the wave power. In some embodiments, an ultrasonic transducer (e.g., ultrasonic transducer 108) of implantable device 304 can be configured to receive the powering ultrasonic waves. In some embodiments, implantable device 304 can include two or more ultrasonic transducers configured to receive corresponding portions of the powering ultrasonic waves. As discussed above, implementing two or more ultrasonic transducers may enable implantable device 304 to more consistently and efficiently extract power from the powering ultrasonic waves, according to some embodiments.

In step 318, implantable device 304 converts energy from the powering ultrasonic waves into an electrical signal to power implantable device 304. In some embodiments, implantable device 304 includes one or more ultrasonic transducers (e.g., ultrasonic transducer 108) configured to convert mechanical energy of the received powering ultrasonic waves into the electrical signal having electrical energy. In some embodiments, implantable device 304 can be fully powered based on the powering ultrasonic waves generated by interrogator 302.

In step 320, implantable device 304 transmits, to interrogator 302, information that indicates whether more power or less power should be transmitted to implantable device 304. In some embodiments, a controller circuit (e.g., controller circuit 120) of implantable device 304 can be configured to generate the information. For ease of explanation, the following steps may refer to such information as power information. In some embodiments, step 320 can include one or more of steps 322-330.

In step 322, implantable device 304 receives the communication ultrasonic waves from interrogator 302. In some embodiments, the ultrasonic transducer (e.g., ultrasonic transducer 108) can be configured to generate an electrical signal based on the received communication ultrasonic waves. In some embodiments, a demodulation circuit (e.g., in modulation and demodulation circuit 112) of implantable device 304 can be configured to extract an instruction from the communication ultrasonic waves that requests implantable device 304 to transmit the power information. For example, the modulation circuit may demodulate the communication ultrasonic waves to extract the instruction.

In step 324, implantable device 304 determines an available power on implantable device 304. In some embodiments, a power monitor (e.g., power monitor 124) of implantable device 304 can be configured to determine the available power. In some embodiments, the available power includes power supplied by the powering ultrasonic waves as received at the ultrasonic transducer (e.g., ultrasonic transducer 108) and power accessible from an energy storage device (e.g., energy storage device 136) on implantable device 304 (e.g., at power circuit 130).

In some embodiments, as described above with respect to power circuit 130, the energy storage device can be configured to operate in at least two power modes to enable implantable device 304 to more efficiently utilize power of the powering ultrasonic waves and to provide consistent power to implantable device 304. In some embodiments, the power modes include a discharging mode in which a portion of energy stored at the energy storage device is discharged to convey power from the energy storage device to power implantable device 304 (e.g., one or more load circuits). In some embodiments, the power modes include a charging mode in which a portion of power of the powering ultrasonic waves is conveyed to the energy storage device capable of storing energy.

In some embodiments, the power monitor can be configured to determine the available power based on determining a maximum voltage (i.e., an open-circuit voltage) provided by the ultrasonic transducer. In some embodiments, the maximum voltage corresponds to a maximum possible voltage of the electrical signal. In some embodiments, implantable device 304 includes a voltage sensor configured to measure data corresponding to the maximum voltage of the ultrasonic transducer. For example, the voltage sensor may be a voltage divider coupled to the electrical signal. In some embodiments, the power monitor can determine the maximum voltage based on the data received from the voltage sensor.

In some embodiments, the power monitor can be configured to determine the available power based on energy stored at the energy storage device. For example, the power monitor may determine the stored energy based on a voltage or an electrical current of the energy storage device as measured by a sensor. In some embodiments, the power monitor is configured to determine the available power based on a rate of change of the energy stored at the energy storage device.

In some embodiments, implantable device 304 includes a power conveyor circuit (e.g., power conveyor circuit 134) configured to convert a first voltage associated with the electrical signal, as generated by the ultrasonic transducer, to a second voltage to power implantable device 304 and its load circuits. In some embodiments, the power conveyor circuit includes a charge pump configured to convert the first voltage to the second voltage having a greater magnitude than the first voltage. In some embodiments, to generate the second voltage, the controller circuit can be configured to control one or more switches of the charge pump to control a plurality of capacitors (of the charge pump). As described above, this conversion may be needed because an intensity of the powering ultrasonic waves may be limited below a certain value (e.g., by government regulations) to ensure human safety, which may result in the first voltage having too low of a voltage to power the load circuits of implantable device 304. In some embodiments, the power monitor can be configured to determine the available power based on a switching frequency of at least one of the one or more switches of the charge pump.

In step 326, implantable device 304 determines a consumed power at implantable device 304. In some embodiments, the power monitor (e.g., power monitor 124) of implantable device 304 can be configured to determine the consumed power.

In some embodiments, the power consumption can include power consumed by one or more load circuits on implantable device 304. In some embodiments, to determine the consumed power, the power monitor can be configured to detect a current value of an electrical current driving one or more load circuits of implantable device 304. For example, the power monitor may receive data from a current sensor indicating the current value.

In some embodiments, implantable device 304 can determine the consumed power based on an operating mode of implantable device 304. In some embodiments, implantable device 304 can be configured to store in a non-transitory memory (e.g., memory 126) an estimate consumed power corresponding to each operating mode. For example, implantable device 304 may include a nerve-stimulation mode and a temperature-recording mode. In this example, implantable device 304 may store a higher estimate consumed power for the nerve-stimulation mode than that for the temperature-recording mode because inducing an electrical pulse to stimulate a nerve requires more power than storing a detected temperature.

In step 328, implantable device 304 generates the power information based on the available power and the consumed power. In some embodiments, the power information includes information indicating the available power, the consumed power, or a combination thereof.

In some embodiments, the power information can include a request for either more power or less power and generated based on the available power and the consumed power. In some embodiments, the power information can include a request to maintain the same power. In some embodiments, the power information can include a request that indicates an amount of power to be increased or decreased. For example, the power monitor (e.g., power monitor 124) of implantable device 304 may be configured to compare the available power with the consumed power to generate the request. In some embodiments, implantable device 304 can generate the power information by performing method 400 of FIG. 4, as will be described below.

In step 330, implantable device 304 emits an ultrasonic backscatter of the communication ultrasonic wave with the ultrasonic backscatter encoding the power information. In some embodiments, the controller circuit can be configured to control a modulation circuit (e.g., in modulation and demodulation circuit 112) of implantable device 304 to modulate an electrical current supplied by the electrical signal corresponding to the communication ultrasonic waves to encode the power information. In some embodiments where implantable device 304 includes a plurality of ultrasonic transducers, the controller circuit can be configured to select one or more of the ultrasonic transducers to emit the ultrasonic backscatter having encoded information. In some embodiments, the controller circuit can be configured to select the one or more ultrasonic transducers based on one or more transducer parameters. For example, such transducer parameters may include a voltage, an electrical current, a power, etc.

In step 312, interrogator 302 (e.g., transducer circuit 204) receives the power information from implantable device 304. In some embodiments, interrogator 302 can be configured to receive the ultrasonic backscatter corresponding to the transmitted communication ultrasonic waves of step 310. In some embodiments, a data processor (e.g., data processor 211) of interrogator 302 can be configured to extract the power information from the ultrasonic backscatter received at one or more ultrasonic transducers of interrogator 302.

In step 314, interrogator 302 determines whether to adjust the wave power based on the power information. In some embodiments, to adjust the wave power, a controller circuit (e.g., controller circuit 212) of interrogator 302 can be configured to set the one or more ultrasonic wave settings to control the wave power to correspond to the power information. For example, as shown in FIG. 3, method 300 may proceed back to step 306. Subsequently, interrogator 302 may generate and transmit second powering ultrasonic waves having a second wave power based on the power information, according to some embodiments. Implantable device 304 may then receive the second powering ultrasonic waves with the second wave power to enable safe operation and consistent power.

In some embodiments, the power information includes a request for more power or less power to be transmitted to implantable device 304. In these embodiments, the controller circuit can be configured to set the one or more ultrasonic wave settings to control the wave power to correspond to the request. For example, if the request is for more power, interrogator 302 may increase an instantaneous intensity value (i.e., an example of an ultrasonic wave setting), increase a pulse width (i.e., another example of an ultrasonic wave setting), or increase both the instantaneous intensity value and the pulse width.

In some embodiments, the power information includes information indicating the available power and consumed power of implantable device 304. In these embodiments, the controller circuit can be configured to determine whether more power or less power should be transmitted to implantable device 304 based on the power information. In some embodiments, the controller circuit of interrogator 302 can be configured to make such a determination by performing method 400 of FIG. 4, as will be described below.

In some embodiments, as described above, the powering ultrasonic waves can be transmitted as a PWM signal. In some embodiments, to control a wave power of the powering ultrasonic waves, interrogator 302 can be configured to set one or more ultrasonic wave settings such as an instantaneous intensity value or a pulse width of the PWM signal. In some embodiments, interrogator 302 can be configured to set both the instantaneous intensity value and the pulse width of the PWM signal.

Figure 4:
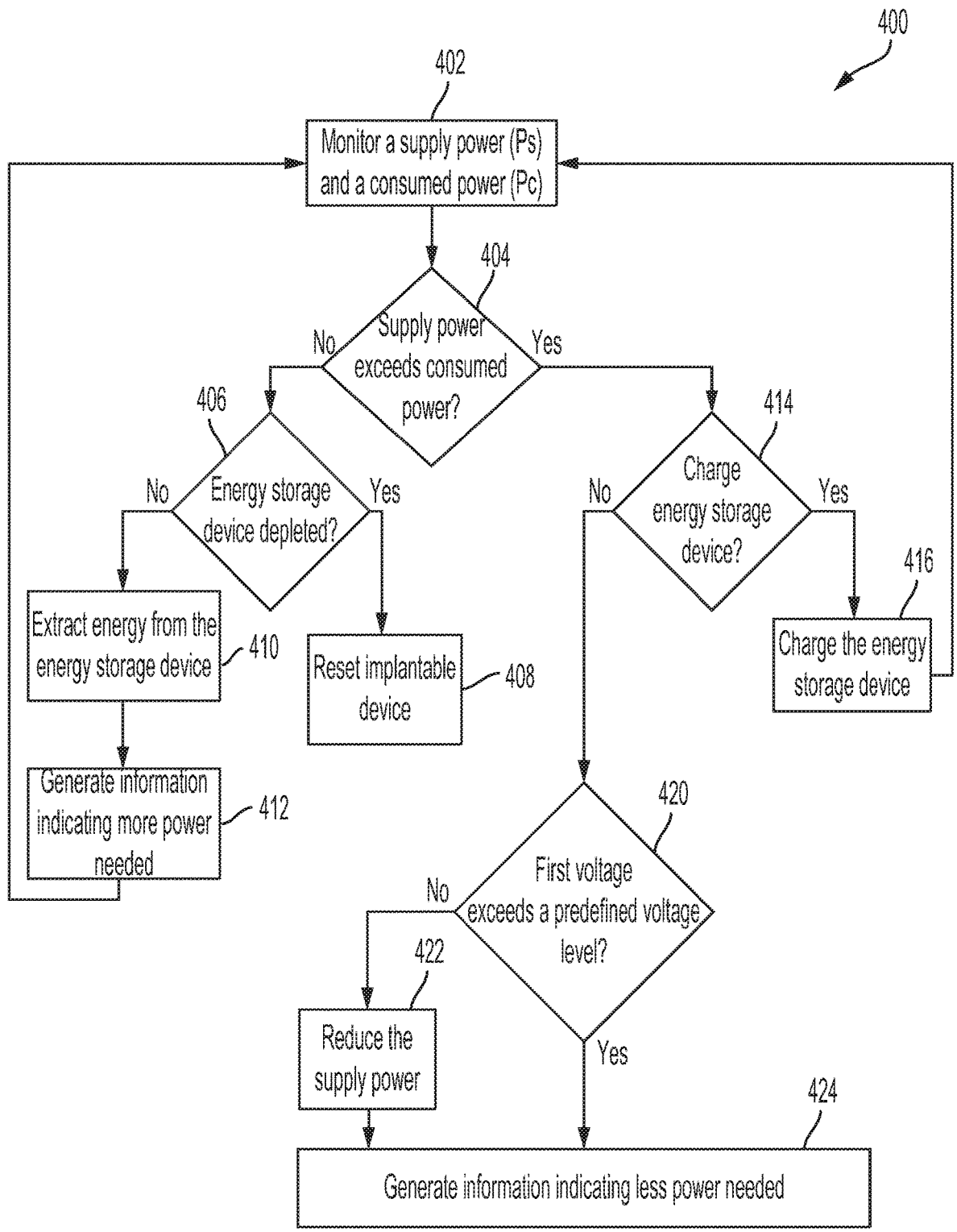
FIG. 4 illustrates a method for determining information that indicates whether more power or less power should be transmitted from an interrogator to an implantable device, according to some embodiments.

FIG. 4 illustrates a method 400 for determining information that indicates whether more power or less power should be transmitted from an interrogator to an implantable device, according to some embodiments. In some embodiments, the implantable device may be an example of implantable device 104 of FIG. 1 or implantable device 304 of FIG. 3. In some embodiments, the interrogator may be an example of interrogator 202 of FIG. 2 or interrogator 302 of FIG. 3. In some embodiments, method 400 can be performed at the implantable device, as will be further described below. In other embodiments, method 400 can be performed at the interrogator, as will be further described below. For ease of explanation, various steps below of method 400 may refer to components of implantable device 104 as described with respect to FIG. 1, components of interrogator as described with respect to FIG. 2, or steps of method 300 as described with respect to FIG. 3.

In step 402, a consumed power (Pc) of the implantable device and a supply power (Ps) associated with a first voltage and the implantable device is monitored. As described above with respect to step 318, an ultrasonic transducer of the implantable device can convert energy from received powering ultrasonic waves into an electrical signal to power the implantable device. In some embodiments, the supply power corresponds to power provided by the electrical signal, as described above in step 324.

In some embodiments, the implantable device can be configured to determine the supply power based on the electrical signal generated by the ultrasonic transducer. In some embodiments, a power monitor (e.g., power monitor 124) can be configured to determine the supply power based on determining a maximum voltage (i.e., an open-circuit voltage) provided by the ultrasonic transducer. In some embodiments, the maximum voltage corresponds to a maximum possible voltage of the electrical signal. In some embodiments, the implantable device includes a voltage sensor configured to measure data corresponding to the maximum voltage of the ultrasonic transducer. For example, the voltage sensor may be a voltage divider coupled to the electrical signal. In some embodiments, the power monitor can determine the maximum voltage based on the data received from the voltage sensor.

In some embodiments, the implantable device can be configured to determine the consumed power based on an operating mode of the implantable device. In some embodiments, the implantable device can be configured to dynamically determine the power consumption of the implantable device based on one or more detected voltages or electrical currents of one or more load circuits of the implantable device.

In some embodiments, the implantable device includes a power conveyor circuit (e.g., power conveyor circuit 134) that receives a first voltage at a first voltage node based on the electrical signal and converts the first voltage into a second voltage to power the implantable device. For example, the power conveyor circuit may include a charge pump that controls a plurality of capacitors to provide the second voltage greater in magnitude than the first voltage. As discussed above, the second voltage may be needed because the first voltage provided by the electrical signal generated from the powering ultrasonic waves may be too low to operate the various electronic components (e.g., transistors). In some embodiments, the power conveyor circuit generates an output electrical signal having the second voltage to power the load circuits of the implantable device. In these embodiments, the implantable device can be configured to determine the power consumption based on the second voltage and an electrical current of the output electrical signal. Accordingly, the consumed power may be associated with the second voltage provided by the power conveyor circuit, according to some embodiments.

In some embodiments, where method 400 is performed at the interrogator, the interrogator can receive power information from the implantable device and indicating the supply power and the consumed power.

In step 404, whether the supply power exceeds the consumed power is determined. If the supply power is determined to exceed the consumed power, method 400 proceeds to step 414. Otherwise, method 400 proceeds to step 406. In some embodiments, the implantable device (e.g., power monitor 124) can be configured to compare the monitored supply power with the monitored consumed power to make this determination.

In some embodiments, where method 400 is performed at the interrogator, the interrogator can receive power information from the implantable device and indicating the supply power and the consumed power. Based on this information, the interrogator (e.g., controller circuit 212) can make a similar comparison to determine whether the supply power exceeds the consumed power.

In step 406, whether an energy storage device of the implantable device is depleted is determined. In some embodiments, if information indicating that an amount of energy stored at the energy storage device falls below a first predefined level, the energy storage device can be determined to be depleted. In some embodiments where the energy storage device includes a capacitor, the implantable device can determine information corresponding to the amount of stored energy based on a current voltage (V) of the capacitor. This is because the amount of energy (E) stored on the capacitor is based on a capacitance (C) of the capacitor and a current voltage (V) of the capacitor (e.g., $E=\frac{1}{2} CV^2$). In some embodiments, the implantable device can compare the information (e.g., a voltage) of the energy storage device with the first predefined level to determine whether the energy storage device is depleted. If the energy storage device is determined to be depleted, method 400 proceeds to step 408. Otherwise, method 400 proceeds to step 410.

In some embodiments, where method 400 is performed at the interrogator, the interrogator can perform a similar comparison between the information of the energy storage device and the first predefined level, as described above. For example, interrogator may extract the information from an ultrasonic backscatter emitted by the implantable device, as described above with respect to step 312.

In step 408, the implantable device is reset. In some embodiments, the implantable device can generate an alarm indicating a power on reset (POR) condition because there is not enough available power at the implantable device to power its load circuits. In some embodiments, this alarm can be included in the information transmitted to the interrogator, as described above with respect to step 320.

In some embodiments, where method 400 is performed at the interrogator, the interrogator can receive, from the implantable device, power information including the alarm indicating the POR condition. In some embodiments, based on the alarm, the interrogator can be configured to select one or more wave parameters to retransmit powering ultrasonic waves to power up the implantable device. For example, the alarm may cause the interrogator to transmit the powering ultrasonic waves for a predetermined amount of time to reinitiate a power up or startup mode of the implantable device. In some embodiments, the power up mode may include resetting counters and setting operation logic (e.g., FSM states) to be in an initialization state.

In step 410, energy is extracted from the energy storage device to power the implantable device. As described above with respect to FIG. 1, the energy storage device can be configured to operate in at least two power modes to enable the implantable device to more efficiently utilize power of the powering ultrasonic waves and to provide consistent power to its load circuits, according to some embodiments. In some embodiments, the power modes include a discharging mode in which a portion energy stored at the energy storage device is discharged to convey power from the energy storage device to power one or more load circuits of the implantable device.

In some embodiments, a controller circuit (e.g., controller circuit 120) of the implantable device can be configured to control the power conveyor circuit to discharge the energy storage device to extract the energy. In some embodiments, the energy storage device can be configured to be electrically coupled to the power conveyor circuit such that discharging the energy storage device increases the first voltage at the first voltage node of the power conveyor circuit.

In some embodiments, the power conveyor circuit can be configured to operate the energy storage device in the discharging mode. In some embodiments, whether the energy storage device is depleted can be periodically monitored and the power conveyor circuit can be configured to convey power from the energy storage device as long as it is not depleted.

In some embodiments, where method 400 is performed at the interrogator, the interrogator can generate an instruction to request the implantable device to control the power conveyor circuit to discharge the energy storage device to extract the energy. In some embodiments, the interrogator can be configured to encode the instruction in communication ultrasonic waves transmitted by an ultrasonic transducer circuit (e.g., ultrasonic transducer circuit 204) to communicate with the implantable device.

In step 412, information indicating more power needed is generated. In some embodiments, the implantable device can be configured to generate the power information, as described above with respect to step 320. For example, the power information may include a request for more power to be transmitted to the implantable device. In another example, the power information may include an amount of additional power to be provided by the implantable device. Subsequently, as described above with respect to FIG. 3, the power information may be transmitted to the interrogator configured to generate second powering waves having a second wave power corresponding to the power information indicating more needed power. In some embodiments, method 400 proceeds back to step 402 where the supply power and the consumed power are monitored.

In some embodiments, where method 400 is performed at the interrogator, the interrogator can generate information associated with one or more ultrasonic wave settings to increase the wave power of transmitted powering ultrasonic waves.

In step 414, whether the energy storage device of the implantable device should be charged is determined. In some embodiments, the implantable device can determine to charge the energy storage device if the energy storage device is not fully charged.

In some embodiments, step 414 can correspond to step 406, as described above where the same determination is performed. In some embodiments, if information indicating that an amount of energy stored at the energy storage device falls below the first predefined level, the energy storage device can be determined to be depleted and therefore not fully charged. If the energy storage device is determined to be depleted, method 400 proceeds to step 416. Otherwise, method 400 proceeds to step 420.

In some embodiments, if information indicating that an amount of energy stored at the energy storage device exceeds a second predefined level, the energy storage device can be determined to be fully charged. In some embodiments, the second predefined level exceeds the first predefined level. In some embodiments where the energy storage device includes a capacitor, the implantable device can determine information corresponding to the amount of stored energy based on a current voltage (V) of the capacitor. This is because the amount of energy (E) stored on the capacitor is based on a capacitance (C) of the capacitor and a current voltage (V) of the capacitor (e.g., $E=\frac{1}{2} CV^2$). In some embodiments, the implantable device can compare the information (e.g., a voltage) of the energy storage device with the second predefined level to determine whether the energy storage device is fully charged. If the energy storage device is determined to be fully charged, method 400 proceeds to step 420. Otherwise, method 400 proceeds to step 416.

In some embodiments, the power conveyor circuit can be configured to operate the energy storage device in the charging mode. In some embodiments, whether the energy storage device is fully charged can be periodically monitored and the power conveyor circuit can be configured to convey a portion of the supply power to charge the energy storage device as long as the energy storage device is not fully charged.

In some embodiments, where method 400 is performed at the interrogator, the interrogator can perform a similar comparison between the information of the energy storage device and the first predefined level or the second predefined level, as described above. For example, interrogator may extract the information from an ultrasonic backscatter emitted by the implantable device, as described above with respect to step 312.

In step 416, the energy storage device is charged. In some embodiments, as described above with respect to FIG. 1, the energy storage device can be configured to operate in at least two power modes to enable the implantable device to more efficiently utilize power of the powering ultrasonic waves and to provide consistent power to its load circuits. In some embodiments, the power modes include a charging mode in which a portion of the supply power is conveyed to the energy storage device capable of storing energy.

In some embodiments, the controller circuit can be configured to control the power conveyor circuit to charge the energy storage device to utilize the excess power provided by the supply power. In some embodiments, the energy storage device can be configured to be electrically coupled to the power conveyor circuit such that charging the energy storage device reduces the first voltage at the first voltage node of the power conveyor circuit.

In some embodiments, where method 400 is performed at the interrogator, the interrogator can generate an instruction to request the implantable device to control the power conveyor circuit to charge the energy storage device to utilize the excess power supply. In some embodiments, the interrogator can be configured to encode the instruction in communication ultrasonic waves transmitted by an ultrasonic transducer circuit (e.g., ultrasonic transducer circuit 204) to communicate with the implantable device.

In step 420, whether the first voltage exceeds a predefined voltage level is determined. In some embodiments, the predefined voltage level corresponds to maximum allowable supply voltage (e.g., less than 4V, 5 V, or 6V) to maintain safe operation of the implantable device. By maintain the first voltage below the predefined voltage level, the implantable device may be safeguarded from overheating and/or damaging the electrical components within the implantable device. In some embodiments, the controller circuit of the interrogator can be configured to determine whether the first voltage exceeds the predefined voltage level. If the first voltage is determined to exceed the predefined voltage level, method 400 proceeds to step 422. Otherwise, method 400 proceeds to step 424.

In some embodiments, where method 400 is performed at the interrogator, the interrogator can perform a similar comparison between the first voltage and the predefined voltage level, as described above. For example, interrogator may extract information from an ultrasonic backscatter emitted by the implantable device, as described above with respect to step 312, and the information may include the first voltage.

In step 422, the supply power is reduced at the implantable device. In some embodiments, the implantable device can be configured to control one or more switches configured to generate the electrical signal from the powering ultrasonic waves to reduce the supply power. In some embodiments, the one or more switches includes a switch to control a rectifying circuit that converts the electrical signal in an alternative current (AC) form to a direct current (DC) form corresponding to the first voltage. In some embodiments, the implantable device can be configured to open the switch to prevent the power supply from powering the load circuits of the implantable device. In some embodiments, the one or more switches can include a switch configured to shunt the ultrasonic transducer. In some embodiments, by shunting the leads of the ultrasonic transducer (e.g., causing a short circuit), an amount of backscattered energy can be changed to reduce the supply power.

In step 424, information indicating less power needed is generated. In some embodiments, the implantable device can be configured to generate the power information, as described above with respect to step 320. For example, the power information may include a request for less power to be transmitted to the implantable device. In another example, the power information may include an amount of decreased power to be provided by the implantable device. Subsequently, as described above with respect to FIG. 3, the power information may be transmitted to the interrogator configured to generate second powering waves having a second wave power corresponding to the power information indicating less needed power. In some embodiments, method 400 proceeds back to step 402 where the supply power and the consumed power are monitored.

In some embodiments, where method 400 is performed at the interrogator, the interrogator can generate information associated with one or more ultrasonic wave settings to decrease the wave power of transmitted powering ultrasonic waves.

Figure 5:
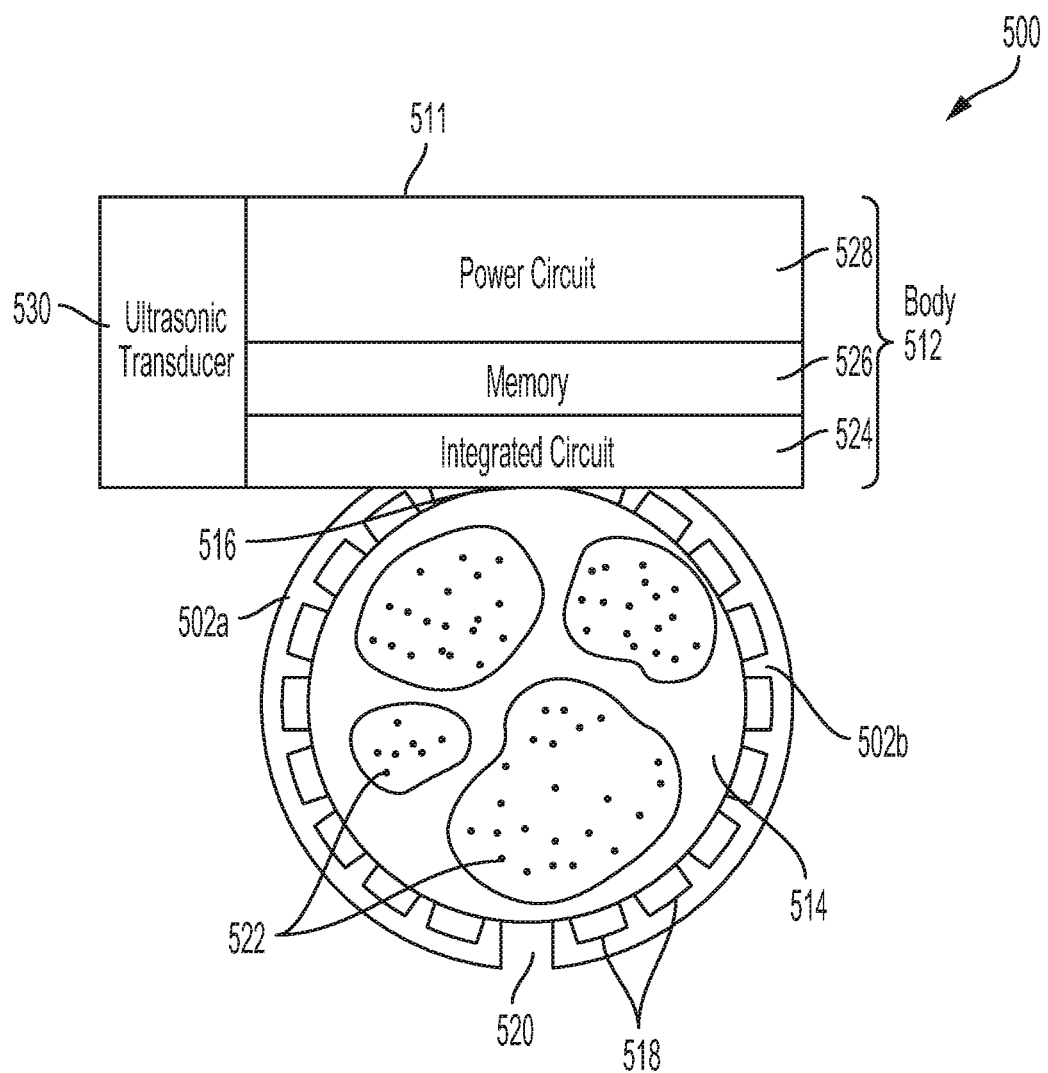
FIG. 5 illustrates a diagram of an implantable device configured to interact with a nerve of a subject, according to some embodiments.

FIG. 5 illustrates a diagram 500 of an implantable device 511 configured to interact with a nerve 514 of a subject, according to some embodiments. In some embodiments, implantable device 511 can be an example implementation of implantable device 104 as described above with respect to FIG. 1. As shown in diagram 500, implantable device 511 can be implanted on nerve 514 and include one or more curved member such as curved member 502 extending from a body 512. Body 512 of implantable device 511 can include integrated circuit 524 (including, e.g., modulation and demodulation circuit 112, stimulation circuit 114, detection circuit 116, or controller circuit 120), a non-transitory memory 526 (e.g., memory 126), a power circuit 528 (e.g., power circuit 130), and an ultrasonic transducer 530 (e.g., ultrasonic transducer 108 or ultrasonic transducer circuit 106). In some embodiments, body 512 includes a plurality of ultrasonic transducers including ultrasonic transducer 530. Accordingly, it is to be understood that ultrasonic transducer 530, as shown in diagram 500, may represent a plurality of ultrasonic transducers.

In some embodiments, ultrasonic transducer 530 can be configured to receive ultrasonic waves transmitted by an interrogator (e.g., interrogator 102 of FIG. 1 or interrogator 202 of FIG. 2) and convert the mechanical energy of the ultrasonic waves into electrical energy to power implantable device 511. For example, ultrasonic transducer 530 may convert the mechanical energy of the ultrasonic waves into an electrical signal that is processed by power circuit 528.

In some embodiments, power circuit 528 can include a power conveyor circuit (e.g., power conveyor circuit 134) configured to convert the electrical signal having a first voltage to a second signal having a second voltage to power various components of integrated circuit 524. In some embodiments, power circuit 528 can include a rectifying circuit (e.g., an active rectifier) to convert the electrical signal in an AC form to a DC form where the converted electrical signal may be associated with the first voltage. In some embodiments, the power conveyor circuit can include a charge pump to generate the second voltage greater than the first voltage. In some embodiments, power circuit 528 can include an energy storage device (e.g., energy storage device 136) configured to store excess energy provided by the electrical signal and to operate as a secondary power source if the power supplied by the interrogator is insufficient. In some embodiments, the power conveyor circuit can be configured to control whether power is to be conveyed to or from the energy storage device, which effectively charges or discharges the energy storage device, respectively. In some embodiments, the power conveyor circuit can be configured control an amount of time (e.g., a number of clock cycles) that the power is conveyed in addition to the direction of power flow (e.g., in forward flow or in reverse flow).

In some embodiments, integrated circuit 524 includes a controller circuit (e.g., controller circuit 120) configured to generate information indicating whether more power or less power should be transmitted to the interrogator. In some embodiments, the controller circuit can be configured to generate this power information based on the available power as supplied by power circuit 528 and a power consumed by integrated circuit 524. In some embodiments, the available power includes the supply power provided by ultrasonic transducer 530 and accessible power provided by the energy storage device of power circuit 528. In some embodiments, the controller circuit can be configured to control ultrasonic transducer 530 to transmit to the interrogator the generated power information to cause the interrogator to control the wave power of transmitted ultrasonic waves.

In some embodiments, the consumed power can be determined by the controller circuit based on an operating mode of implantable device 511, as described above with respect to FIGS. 1 and 3. Examples of the operating mode may be a stimulation mode or a detection mode, each of which may operate electrode pads 518 on curved member 502.

In some embodiments, in the detection mode, electrode pads 518 are configured to detect an electrophysiological signal, and a detection signal based on the electrophysiological signal is received by integrated circuit 524. The detection signal received by integrated circuit 524 may be processed (for example, amplified, digitized, and/or filtered) by a detection circuit (e.g., by detection circuit 116) before being received by the controller circuit. In some embodiments, the controller circuit can access non-transitory memory (e.g., memory 126) to store data related to the detected electrophysiological signal.

In some embodiments, in the stimulation mode, the controller circuit can generate a stimulation signal based on the detection signal, and operate one or more electrode pads 518 to emit an electrical pulse to nerve 514 based on the stimulation signal. In some embodiments, the controller circuit can access the non-transitory memory (e.g., memory 126) to store data related to the stimulation signal or electrical pulse emitted to nerve 514. Data stored on the non-transitory memory can be wirelessly transmitted through ultrasonic backscatter waves emitted by ultrasonic transducer 530. As described above with respect to FIG. 1, to transmit data using the ultrasonic backscatter, ultrasonic transducer 530 may first receive ultrasonic waves and generates an electrical current that flows through a modulation circuit. Then, the controller circuit may access the memory and operate the modulation circuit to modulate the electrical current flowing through the modulation circuit to encode the data. Through such a process, the ultrasonic backscatter waves emitted by ultrasonic transducer 530 can encode the data.

In some embodiments, as shown in diagram 500, curved member 502 can include a first portion 502a and a second portion 502b bridged by body 512 at point 516. In some embodiments, first portion 502a and second portion 502b are directly connected, and curved member 502 is attached to body 512 through a connecting member. Curved member 502 can include a plurality of electrode pads 518 on the inner surface of curved member 502, and electrode pads 518 can be radially positioned around an axis parallel to the length of nerve 514. A separation 520 between first portion 202a and second portion 202b is present along curved member 502 (which may be similarly present in other curved members of implantable device 511). In some embodiments, implantable device 511 can be implanted by flexing first portion 502a and second portion 502b of curved member 502 outwardly, thereby expanding the size of the separation and allowing nerve 514 or other filamentous tissue to pass through separation 520 and fit within the cylindrical space formed by curved member 502. First portion 502a and second portion 502b of curved member 502 can be released, which allows curved member 502 to wrap around nerve 514 or other filamentous tissue.

The plurality of electrode pads 518 of as shown in FIG. 5 are outside of nerve 514, but in direct contact with the epineurium of nerve 514. Nerve 514 can include several fascicles 522. In some embodiments, electrode pads 518 within curved member 502 can be operated for targeted emission of an electrical pulse to one or more of fascicles 522 or other subset of nerve fibers, and/or operated for targeted detection of an electrophysiological signal transmitted by one or more of fascicles 522 or other subset of nerve fibers. For example, electrode pads 518 can be selectively activated by the controller circuit within integrated circuit 524, which is housed within body 512, to emit an electric pulse targeted to one or more fascicles 522. In another example, electrode pads 518 are operated by the controller circuit to detect an electrophysiological signal transmitted by one or more of fascicles 522 within nerve 514. In some embodiment, curved member 502 can be configured to detect the electrophysiological signal transmitted by nerve 514 or a subset of nerve fibers, emit an electrical pulse to nerve 514 or targeted to a subset of nerve fibers, or both detect the electrophysiological signal transmitted by nerve 514 or a subset of nerve fibers and emit an electrical pulse to nerve 514 or targeted to a subset of nerve fibers. For example, implantable device 511 may include a plurality of curved members (including curved member 502) in which a first curved member can be configured to detect the electrophysiological signal transmitted by nerve 514 or a subset of nerve fibers, and a second curved member can be configured to emit an electrical pulse to nerve 514 or targeted to a subset of nerve fibers.

In some embodiments, curved member 502 can be sized to engage a selected nerve 514 or fibrous tissue containing nerve 514. Nerve 514 can be the spinal cord or a peripheral nerve. In some embodiments, nerve 514 is an autonomic nerve or a somatic nerve. In some embodiments, nerve 514 is a sympathetic nerve or a parasympathetic nerve. In some embodiments, nerve 514 is a vagus nerve, a mesenteric nerve, a splenic nerve, a sciatic nerve, a tibial nerve, a pudendal nerve, a celiac ganglion, a sacral nerve, or any branch thereof.

The size, shape, and spacing of curved member 502 on implantable device 511 can depend on the type and size of tissue that implantable device 511 engages. In some embodiments, two or more curved members of implantable device 511 are spaced by about 0.25 mm or more (such as about 0.5 mm or more, about 1 mm or more, about 2 mm or more, about 3 mm or more, about 4 mm or more, about 5 mm or more, about 6 mm or more, or about 7 mm or more). In some embodiments, the two or more curved members are space by about 8 mm or less (such as about 7 mm or less, about 6 mm or less, about 5 mm or less, about 4 mm or less, about 3 mm or less, about 2 mm or less, about 1 mm or less, or about 0.5 mm or less). By way of example, the two or more curved members can be spaced about 0.25 mm to about 0.5 mm, about 0.5 mm to about 1 mm, about 1 mm to about 2 mm, about 2 mm to about 3 mm, about 3 mm to about 4 mm, about 4 mm to about 5 mm, about 5 mm to about 6 mm, about 5 mm to about 7 mm, or about 7 mm to about 8 mm apart. The width of curved member 502 can also vary depending on the application of implantable device 511 or the tissue engaged by implantable device 511. In some embodiments, the width of curved member 502 is about 100 µm or more (such as about 150 µm or more, about 250 µm or more, about 500 µm or more, about 1 mm or more, or about 1.5 mm or more). In some embodiments, the width of curved member 502 is about 2 mm or less (such as about 1.5 mm or less, about 1 mm or less, about 500 µm or less, about 250 µm or less, or about 150 µm or less. In some embodiments, the width of curved members 502 is about 100 µm to about 2 mm (such as about 100 µm to about 150 µm, about 150 µm to about 250 µm, about 250 µm to about 500 µm, about 500 µm to about 1 mm, about 1 mm to about 1.5 mm, or about 1.5 mm to about 2 mm). The inner surface of curved member 502 form a cylindrical space through which nerve 514 and/or filamentous tissue passes. The diameter of the cylindrical space formed by curved member 502 depends on the target nerve and/or filamentous tissue that implantable device 511 will engage. In some embodiments, curved member 502 forms a cylindrical space with a diameter of about 50 µm to about 15 mm (for example, about 50 µm to about 100 µm, about 100 µm to about 250 µm, about 250 µm to about 500 µm, about 500 µm to about 1 mm, about 1 mm to about 1.5 mm, about 1.5 mm to about 2.5 mm, about 2.5 mm to about 5 mm, about 5 mm to about 10 mm, or about 10 mm to about 15 mm).

In some embodiments, implantable device 511 includes one or more additional securing members configured to secure implantable device 511 to the filamentous tissue. Such securing members can include, for example, loops for suturing the implantable device to anatomical structure (such as the filamentous tissue or nerve, or other tissue surrounding the filamentous tissue or nerve), pins, or clamps. For example, implantable device 511 can be sutured to the filamentous tissue or nerve 514, or tissue surrounding the filamentous tissue or nerve, to limit movement of implantable device 511 once implanted.

In some embodiment, curved member 502 of implantable device 511 can include a metal, metal alloy, ceramic, silicon, or a non-polymeric material. Curved member 502 may be flexible, and is preferably sprung such that curved member 502 can be positioned around nerve 514 and/or filamentous tissue. In some embodiments, curved member 502 or a portion of curved member 502 is coated with an elastomeric coating or a non-elastomeric coating, which is preferably bioinert, such as polydimethylsioloxane (PDMS), a silicone, a urethane polymer, a poly(p-xylylene) polymer (such as a poly(p-xylylene) polymer sold under the tradename PARYLENE®), or a polyimide. Curved member 502 can include a plurality of electrode pads 518 on an inner surface. In some embodiments, electrode pads 518 on the inner surface of curved member 502 are not coated with the elastomeric coating or the non-elastomeric polymer coating, although the inner surface may be coated with a conductive material (e.g., electroplated with a PEDOT polymer or a metal to improve electrical characteristics of the electrode pad). Accordingly, in some embodiments, only the outer surface of curved member 502 is coated with the coating. Optionally, the coating further coats the housing of body 512.

In some embodiments, the plurality of electrode pads 518 can include 3, 4, 5, 6, 7, 8, 9, 10, 11, 12, 13, 14, 15, 16, 17, 18, 19, 20, or more electrode pads, such as between about 3 and about 50 electrode pads, between about 3 and about 5 electrode pads, between about 5 and about 10 electrode pads, between about 10 and about 25 electrode pads, or between about 25 and about 50 electrode pads. In some embodiments, the electrode pads within the plurality of electrode pads 518 can be selectively activated by the controller circuit, which allows for targeted electrical pulse emission, as further described herein.

In some embodiments, electrode pads 518 can include any suitable conductive material, such as one or more of (or an alloy of one or more of) tungsten, platinum, palladium, gold, iridium, niobium, tantalum, or titanium. The material of the detecting electrode pads and the stimulating electrode pads may be the same or different. The size and shape of electrode pads 518 may also be the same or different. For example, electrode pads 518 on a given curved member 502 may be of the same or different size, and electrode pads on different curved members may be of the same or different size.

In some embodiments, electrode pads 518 of implantable device 511 are positioned by curved member 502 to be in electrical communication with nerve 514. In some embodiments, electrode pads 518 are not in direct contact with nerve 514 (for example outside and not indirect contact with nerve 514), but are in electrical communication with nerve 514. In some embodiments, electrode pads 518 are positioned within about 2 mm (e.g., within about 1.8 mm, within about 1.6 mm, within about 1.4 mm, within about 1.2 mm, within about 1.0 mm, within about 0.8 mm, within about 0.6 mm, within about 0.4 mm, or within about 0.2 mm) of nerve 514. In some embodiments, electrode pads 518 are configured to penetrate the epineurium of nerve 514 at one or more locations. For example, electrode pads 518 can be needle-shaped, which allows for penetration of the epineurium. In some embodiments, electrode pads 518 directly contact nerve 514, for example the epineurium of nerve 514.

In some embodiments, body 512 includes a housing, which can include a base, one or more sidewalls, and a top. The housing can enclose ultrasonic transducer 530 and integrated circuit 524. The housing may be sealed closed (for example by soldering or laser welding) to prevent interstitial fluid from coming in contact with ultrasonic transducer 530 or integrated circuit 524. The housing is preferably made from a bioinert material, such as a bioinert metal (e.g., steel or titanium) or a bioinert ceramic (e.g., titania or alumina). The housing (or the top of the housing) may be thin to allow ultrasonic waves to penetrate through the housing. In some embodiments, the thickness of the housing is about 100 micormeters ($\mu m$) or less in thickness, such as about 75 $\mu m$ or less, about 50 $\mu m$ or less, about 25 $\mu m$ or less, or about 10 $\mu m$ or less. In some embodiments, the thickness of the housing is about 5 $\mu m$ to about 10 $\mu m$, about 10 $\mu m$ to about 25 $\mu m$, about 25 $\mu m$ to about 50 $\mu m$, about 50 $\mu m$ to about 75 $\mu m$, or about 75 $\mu m$ to about 100 $\mu m$ in thickness.

In some embodiments, body 512 of implantable device 511 is relatively small, which allows for comfortable and long-term implantation while limiting tissue inflammation that is often associated with implantable medical devices. In some embodiments, the longest dimension of body 512 is about 10 mm or less, such as about 5 mm to about 9 mm, or about 6 mm to about 8 mm.

In some embodiments, body 512 includes a material, such as a polymer, within the housing. The material can fill empty space within the housing to reduce acoustic impedance mismatch between the tissue outside of the housing and within the housing. Accordingly, body 512 is preferably void of air or vacuum, according to some embodiments.

In some embodiments, ultrasonic transducer 530 can include a micro machined ultrasonic transducer, such as a capacitive micro-machined ultrasonic transducer (CMUT) or a piezoelectric micro-machined ultrasonic transducer (PMUT), or can include a bulk piezoelectric transducer. Bulk piezoelectric transducers can be any natural or synthetic material, such as a crystal, ceramic, or polymer. Example bulk piezoelectric transducer materials may include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di) fluoride (PVDF), and lead magnesium niobate-lead titanate (PMN-PT).

In some embodiments, the bulk piezoelectric transducer is approximately cubic (i.e., an aspect ratio of about 1:1:1 (length:width:height)). In some embodiments, the piezoelectric transducer is plate-like, with an aspect ratio of about 5:5:1 or greater in either the length or width aspect, such as about 7:5:1 or greater, or about 10:10:1 or greater. In some embodiments, the bulk piezoelectric transducer is long and narrow, with an aspect ratio of about 3:1:1 or greater, with the longest dimension being aligned to the direction of the ultrasonic backscatter waves (i.e., the polarization axis). In some embodiments, one dimension of the bulk piezoelectric transducer is equal to one half of the wavelength ($\lambda$) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 $\mu m$ to about 1000 $\mu m$ (such as about 40 $\mu m$ to about 400 $\mu m$, about 100 $\mu m$ to about 250 $\mu m$, about 250 $\mu m$ to about 500 $\mu m$, or about 500 $\mu m$ to about 1000 $\mu m$). In some embodiments, the height of the piezoelectric transducer is about 5 mm or less (such as about 4 mm or less, about 3 mm or less, about 2 mm or less, about 1 mm or less, about 500 $\mu m$ or less, about 400 $\mu m$ or less, 250 $\mu m$ or less, about 100 $\mu m$ or less, or about 40 $\mu m$ or less). In some embodiments, the height of the piezoelectric transducer is about 20 $\mu m$ or more (such as about 40 $\mu m$ or more, about 100 $\mu m$ or more, about 250 $\mu m$ or more, about 400 $\mu m$ or more, about 500 $\mu m$ or more, about 1 mm or more, about 2 mm or more, about 3 mm or more, or about 4 mm or more) in length.

In some embodiments, ultrasonic transducer 530 has a length of about 5 mm or less (such as about 4 mm or less, about 3 mm or less, about 2 mm or less, about 1 mm or less, about 500 $\mu m$ or less, about 400 $\mu m$ or less, 250 $\mu m$ or less, about 100 $\mu m$ or less, or about 40 $\mu m$ or less) in the longest dimension. In some embodiments, ultrasonic transducer 530 has a length of about 20 $\mu m$ or more (such as about 40 $\mu m$ or more, about 100 $\mu m$ or more, about 250 $\mu m$ or more, about 400 $\mu m$ or more, about 500 $\mu m$ or more, about 1 mm or more, about 2 mm or more, about 3 mm or more, or about 4 mm or more) in the longest dimension.

In some embodiments, ultrasonic transducer 530 is connected to two electrodes to allow electrical communication with integrated circuit 524. The first electrode is attached to a first face of ultrasonic transducer 530 and the second electrode is attached to a second face of ultrasonic transducer 530, with the first face and the second face on opposite sides of ultrasonic transducer 530 along one dimension. In some embodiments, the electrodes include silver, gold, platinum, platinum-black, poly(3,4-ethylenedioxythiophene (PEDOT)), a conductive polymer (such as conductive PDMS or polyimide), or nickel. In some embodiments, the axis between the electrodes of ultrasonic transducer 530 is orthogonal to the motion of ultrasonic transducer 530.

The foregoing description sets forth exemplary methods, parameters and the like. It should be recognized, however, that such description is not intended as a limitation on the scope of the present disclosure but is instead provided as a description of exemplary embodiments. The illustrative embodiments described above are not intended to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. In the foregoing description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the foregoing description uses terms first, second, etc. to describe various elements, these elements should not be limited by the terms. These terms are only used to distinguish one element from another.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The terms "implantable" and "implanted" refer to an object being fully implantable or fully implanted in a subject such that no portion of the object breaches the surface of the subject.

The term "substantially" refers to 90% or more. For example, a curved member that substantially surrounds a cross-section of a nerve refers to a curved member that surrounds 90% or more of the cross-section of the nerve.

The term "subject" and "patient" are used interchangeably herein to refer to a vertebrate animal such as a human.

The terms "treat," "treating," and "treatment" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

In addition, it is also to be understood that the singular forms "a," "an," and "the" used in the foregoing description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

What is claimed is:

1. A method of controlling power provided to a device implantable in a subject, comprising, at the implantable device:
   receiving powering ultrasonic waves from an interrogator, the powering ultrasonic waves having a wave power;
   converting energy from the powering ultrasonic waves into an electrical signal to power the implantable device, wherein the electrical signal generates a first voltage at a first voltage node;
   determining an available power at the implantable device and a power consumed by the implantable device, wherein the available power comprises a supply power provided by the electrical signal;
   determining if the first voltage exceeds a predefined voltage level;
   in response to determining that the first voltage exceeds the predefined voltage level, opening one or more switches configured to generate the electrical signal from the powering ultrasonic waves to reduce the supply power; and
   transmitting to the interrogator information that indicates whether more power or less power should be transmitted to the implantable device, wherein the information is associated with the available power and the consumed power.

2. The method of claim 1, wherein the information comprises a request for either more or less power from the interrogator.

3. The method of claim 2, wherein the request is generated based on an available power at the implantable device and a power consumed by the implantable device.

4. The method of claim 1, wherein transmitting the information comprises:
   receiving communication ultrasonic waves from the interrogator; and
   emitting an ultrasonic backscatter of the communication ultrasonic waves, wherein the ultrasonic backscatter encodes the information.

5. The method of claim 4, wherein emitting the ultrasonic backscatter of the communication ultrasonic waves comprises:
   generating an electrical signal based on the communication ultrasonic waves; and
   modulating the generated electrical signal based on the information, wherein the modulated electrical signal encodes the information into the ultrasonic backscatter.

6. The method of claim 1, comprising receiving second powering ultrasonic waves from the interrogator that is configured to generate the second powering ultrasonic waves to have a second wave power based on the information.

7. The method of claim 1, wherein the powering ultrasonic waves comprise a pulse width modulated (PWM) signal.

8. The method of claim 7, wherein the interrogator is configured to adjust an instantaneous intensity value or a pulse width of the PWM signal based on the information.

9. The method of claim 7, wherein the interrogator is configured to adjust the instantaneous intensity value and the pulse width of the PWM signal based on the information.

10. The method of claim 1, wherein the powering ultrasonic waves are received at an ultrasonic transducer of the implantable device, and wherein determining the available power comprises:
   determining a maximum voltage of the ultrasonic transducer; and
   determining the available power based on the maximum voltage.

11. The method of claim 1, wherein determining the available power comprises:
   charging an energy storage device based on the electrical signal; and
   determining the available power based on energy stored at the energy storage device.

12. The method of claim 11, wherein the available power is determined based on a rate of change of the energy stored at the energy storage device.

13. The method of claim 1, wherein determining the available power comprises:
   controlling one or more switches to control a plurality of capacitors configured to convert the first voltage into a second voltage to power the implantable device; and
   determining the available power based on a switching frequency of at least one of the one or more switches.

14. The method of claim 1, wherein determining the consumed power comprises:
   determining the consumed power of the implantable device based on an operating mode of the implantable device.

15. The method of claim 1, wherein the consumed power is consumed by a load circuit of the implantable device, and wherein determining the consumed power comprises:
   detecting a current value of an electrical current driving the load circuit; and
   determining the consumed power based on the detected current value.

16. The method of claim 1, comprising determining if the supply power exceeds the consumed power.

17. The method of claim 16, comprising, in response to determining that the supply power exceeds the consumed power, charging an energy storage device based on the first voltage node, wherein charging the energy storage device reduces the first voltage.

18. The method of claim 17, comprising, in response to determining that the supply power is less than the consumed power, discharging the energy storage device through the first voltage node, wherein discharging the energy storage device increases the first voltage.

19. The method of claim 17, comprising determining whether the energy storage device is fully charged.

20. The method of claim 19, comprising, in response to determining that the supply power exceeds the consumed power and that the energy storage device is fully charged, transmitting to the interrogator the information comprising an indication that the implantable device is being over powered.

21. The method of claim 20, wherein the information comprising the indication is configured to be receivable by the interrogator and causes the interrogator to generate second powering ultrasonic waves that have a second wave power that is less than the wave power of the powering ultrasonic waves.

22. The method of claim 16, comprising, in response to determining that the supply power is less than the consumed power, transmitting to the interrogator the information comprising an indication that the implantable device is being under powered.

23. The method of claim 22, wherein the information comprising the indication is configured to be receivable by the interrogator and causes the interrogator to generate second powering ultrasonic waves having a second wave power greater than the wave power of the powering ultrasonic waves.

24. An implantable device, comprising:
   an ultrasonic transducer configured to receive powering ultrasonic waves from an interrogator and convert the powering ultrasonic waves into an electrical signal to power the implantable device, wherein the powering ultrasonic waves have a wave power;
   a first voltage node, wherein the electrical signal generates a first voltage at the first voltage node;
   one or more switches configured to generate the electrical signal from the powering ultrasonic waves;
   a power monitoring circuit configured to determine an available power at the implantable device and a power consumed by the implantable device, wherein the available power comprises a supply power provided by the electrical signal; and
   a controller circuit configured to:
      determine if the first voltage exceeds a predefined voltage level,
      in response to determining that the first voltage exceeds the predefined voltage level, open the one or more switches, and
      generate information that indicates whether more power or less power should be transmitted to the implantable device, and
   wherein the ultrasonic transducer is further configured to transmit the information to the interrogator.

25. An interrogator device, comprising:
   an ultrasonic transducer configured to:
   transmit first powering ultrasonic waves to an implantable device, the first powering ultrasonic waves having a first wave power;
   receive communication ultrasonic waves from the implantable device, wherein the communication ultrasonic waves comprises information indicating whether more power or less power should be transmitted to the implantable device; and
   transmit second powering ultrasonic waves to the implantable device, wherein the second powering ultrasonic waves have a second power based on the information, wherein the second powering ultrasonic waves comprise a pulse width modulated (PWM) signal.

* * * * *